(12) United States Patent
Sandanayaka et al.

(10) Patent No.: US 7,989,480 B2
(45) Date of Patent: Aug. 2, 2011

(54) ARYL AMINO ACID DERIVATIVES AS INHIBITORS FOR TREATING INFLAMMATION

(75) Inventors: Vincent Sandanayaka, Northboro, MA (US); Jasbir Singh, Naperville, IL (US); David Sullins, Mt. Prospect, IL (US); Mark E. Gurney, Grand Rapids, MI (US)

(73) Assignee: Decode Genetics EHF, Reykjavik (IS)

( * ) Notice: Subject to any disclaimer, the term of this patent is extended or adjusted under 35 U.S.C. 154(b) by 553 days.

(21) Appl. No.: 11/833,382

(22) Filed: Aug. 3, 2007

(65) Prior Publication Data

US 2008/0033024 A1    Feb. 7, 2008

Related U.S. Application Data

(60) Provisional application No. 60/821,499, filed on Aug. 4, 2006.

(51) Int. Cl.
*A61K 31/426* (2006.01)
*A61K 31/22* (2006.01)
*A61K 31/195* (2006.01)
*C07D 277/30* (2006.01)
*C07C 229/00* (2006.01)

(52) U.S. Cl. ........ 514/365; 514/549; 514/561; 548/204; 560/38; 562/443

(58) Field of Classification Search .................. 514/365, 514/549, 561; 548/204; 560/38; 562/443
See application file for complete search history.

(56) References Cited

U.S. PATENT DOCUMENTS

| 4,766,121 A * | 8/1988 | Ellis et al. ..................... 514/247 |
| 5,324,718 A | 6/1994 | Loftsson |
| 5,472,954 A | 12/1995 | Loftsson |
| 2005/0043378 A1 | 2/2005 | Axe et al. |
| 2005/0043379 A1 | 2/2005 | Axe et al. |
| 2005/0288341 A1 | 12/2005 | Nag et al. |

FOREIGN PATENT DOCUMENTS

| EP | 0188351 A | 7/1986 |
| JP | 2006241089 A | 9/2006 |
| WO | WO9611192 A | 4/1996 |
| WO | WO2004066964 A | 8/2004 |
| WO | WO2005012296 A | 2/2005 |
| WO | WO2006097809 A | 9/2006 |
| WO | WO 2006/123229 * | 11/2006 |
| WO | WO2006123229 A | 11/2006 |
| WO | WO2007009715 A | 1/2007 |

OTHER PUBLICATIONS

Bovarnick et al. "An Analog of Thyroxine" Journal of the American Chemical Society, 1939, vol. 61, pp. 2472-2474.*
Leeson et al: "Selective thyromimetics. Cardiac-sparing thyroid hormone analogs containing 3'-arylmethyl substituents" Journal of Medicinal Chemistry, vol. 32, No. 2, 1989, pp. 320-336.
Bovarnick et al: "An Analog of Thyroxine" Journal of the American Chemical Society, vol. 61, No. 9, 1939, pp. 2472-2474.
Beilstein Institute for Organic Chemistry, Frankfurt-Main, DE; 1988, Database accession No. BRN:5174469, CAS RN: 120129-99-9; 3,5-di-iodo-3'-[(6-methylpyridin-3-yl)methyl]-L-thyronine and many other compounds, vol. 1, 1988, pp. 3085-3096.
Farghaly, Abdel-Rahman et al.: "Synthesis of Imidazo[1,2-c]pyrazolo[4,3-e]pyrimidines derived from indole and related heterocycles", Monatshefte Fuer Chemie., vol. 137, No. 9, 2006, pp. 1195-1202.
International Search Report and Written Opinion from International Application No. PCT/US2007/075151 completed Jan. 22, 2008 and mailed on Feb. 1, 2008.

* cited by examiner

*Primary Examiner* — Joseph Kosack
(74) *Attorney, Agent, or Firm* — Heslin Rothenberg Farley & Mesiti P.C.

(57) ABSTRACT

The present invention relates to a chemical genus of 3-(triaryl)-2-aminopropanol derivative inhibitors of LTA4H (leukotriene A4 hydrolase) useful for the treatment and prevention of inflammatory diseases and disorders. The compounds have general formula III:

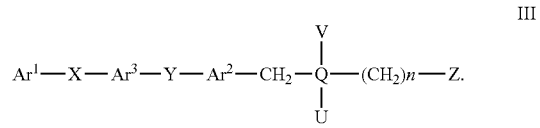

A particular embodiment is

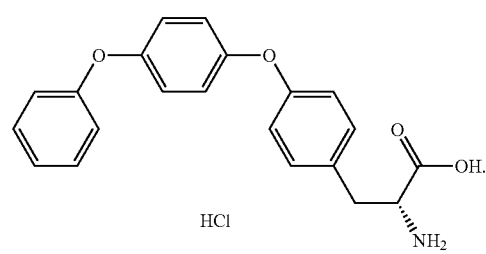

11 Claims, No Drawings

ARYL AMINO ACID DERIVATIVES AS INHIBITORS FOR TREATING INFLAMMATION

RELATED APPLICATIONS

This application claims priority to U.S. Provisional Application No. 60/821,499 filed Aug. 4, 2006, which is hereby incorporated herein by reference in its entirety.

FIELD OF THE INVENTION

The present invention relates to a chemical genus of 3-(triaryl)-2-aminopropanol derivative inhibitors of LTA4H (leukotriene A4 hydrolase) useful for the treatment and prevention of inflammatory diseases and disorders.

BACKGROUND OF THE INVENTION

The end products of the leukotriene pathway are potent inflammatory lipid mediators derived from arachidonic acid. They can potentially contribute to development of atherosclerosis and destabilization of atherosclerotic plaques through lipid oxidation and/or proinflammatory effects. As described elsewhere, a gene on chromosome 13q12 has been identified as playing a major role in myocardial infarction (MI), [Helgadottir et al., *Nature Genetics* doi: 10.1038/ng1311, 8 Feb. 2004]. This gene (ALOX5AP), herein after referred to as an MI disease gene, comprises nucleic acid that encodes 5-lipoxygenase activating protein (FLAP), herein after referred to as FLAP. DNA variants in the FLAP gene increase risk for myocardial infarction by 1.8 fold and for stroke by 1.7 fold. The leukotriene pathway, through FLAP, leads to the production of leukotriene B4 by the enzyme leukotriene A4 hydrolase (LTA4H). Leukotriene B4 is one of the most potent chemokine mediators of arterial inflammation. Particular DNA variants in the gene encoding LTA4H also elevate risk for MI and stroke, as described elsewhere [Hakonarsson et al., *J. Am. Med. Assoc.* 293, 2245-2256 (2005)]. Individuals with a prior history of MI produce more leukotriene B4 when their isolated neutrophils are stimulated with ionomycin. Increased LTB4 production is particularly marked in male patients with a prior history of MI who carry risk variants in the FLAP gene [Helgadottir et al.]. The treatment (prophylactic and/or therapeutic) of certain diseases and conditions (e.g., MI, acute coronary syndrome (ACS), stroke, atherosclerosis) associated with FLAP or with LTA4H can be accomplished by inhibiting LTA4H. Inhibiting LTA4H is advantageous for methods of treatment for MI or susceptibility to MI; for ACS (e.g., unstable angina, non-ST-elevation myocardial infarction (NSTEMI) or ST-elevation myocardial infarction (STEMI)); for decreasing risk of a second MI; for stroke (including transient ischemic attack) or susceptibility to stroke; for atherosclerosis, such as for patients requiring treatment (e.g., angioplasty, stents, coronary artery bypass graft) to restore blood flow in coronary arteries, such as patients requiring treatment for peripheral vascular disease including peripheral occlusive arterial disease, critical limb ischemia (e.g., gangrene, ulceration), and intermittent claudication to restore blood flow in the lower limbs; for atherosclerotic reno-vascular disease; for abdominal aortic aneurysm; and/or for decreasing leukotriene synthesis (e.g., for treatment of MI).

U.S. Patent Application Publication No. 20050043378 and 20050043379, relate to benzooxazol-2-yl, benzothiazol-2-yl and 1H-benzoimidazol-2-yl compounds and derivatives thereof useful as leukotriene A4 hydrolase (LTA4H) inhibitors in treating inflammation and disorders associated with inflammation. These disclosures are incorporated herein by reference as they relate to utility.

SUMMARY OF THE INVENTION

The present invention relates to compounds exhibiting LTA4H enzyme inhibition, having the general formula III

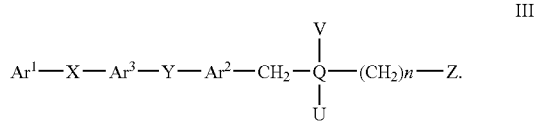

In these compounds, $Ar^1$, $Ar^2$, and $Ar^3$ are selected from aryl, heteroaryl, aryl substituted with from one to three substituents chosen independently from halogen, haloalkyl, hydroxy, loweralkoxy, carboxy, alkoxycarbonyl, aminocarbonyl, cyano, carbonyl, nitro, amino, alkylamino, dialkylamino, mercapto, alkylthio, alkyl sulfoxide, alkyl sulfone and acylamino, and heteroaryl substituted with from one to three substituents chosen independently from halogen, haloalkyl, hydroxy, loweralkoxy, carboxy, alkoxycarbonyl, aminocarbonyl, cyano, carbonyl, nitro, amino, alkylamino, dialkylamino, mercapto, alkylthio, alkyl sulfoxide, alkyl sulfone and acylamino. In these compounds Z is W or —C(=O)W; W is chosen from $OR^2$, $NR^2R^3$, NHOH, N(OH)$R^6$, —N(OH)—C(O)—$R^6$, and CH(OH)C(O)$R^6$, wherein $R^6$ is alkyl; X is chosen from —O—, —S(O)$_{0-2}$—, —$CR^4R^5$—, —C(=O)— and —$NR^4$—. Y is $C_1$-$C_4$ alkylene wherein one or two $CH_2$ may be replaced by —O—, —S(O)$_{0-2}$—, —$CR^4R^5$, C(=O)—, CH(OH) and —$NR^4$—; U is (CH$_2$)$_m$—$NR^1R^2$ or H; m is 0-3; V is (CH$_2$)$_p$—Z or H; p is 0-3; Q is C or N; $R^1$, $R^2$, $R^3$, $R^4$ and $R^5$ are independently chosen from H and alkyl; n is 0-2, with the proviso that when Q is C, both U and V cannot be H, and when Q is N, either U or V is absent and m or p is 2 or 3.

The present invention also relates to a subgenus of compounds of formula III where $Ar^3$ is p-phenylene.

The present invention also relates to compounds having the general formula IV

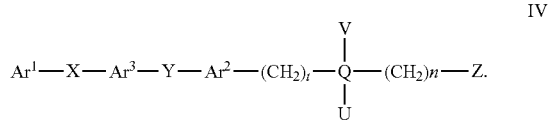

In this compound t is 0 or 1.

A particular subset of the compounds have the formula II:

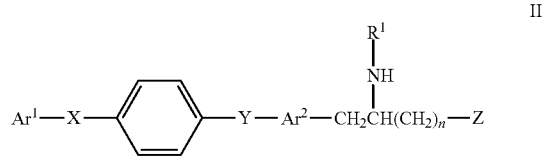

In a third aspect, the invention relates to pharmaceutical compositions comprising a pharmaceutically acceptable carrier and a therapeutically effective amount of at least one compound of the general formulas described above, or an ester, a pharmaceutically acceptable salt or a hydrate of the compounds.

A fourth aspect of the present invention relates to a method for inhibiting leukotriene A4 hydrolase comprising contacting the LTA4H enzyme with a therapeutically effective amount of a compound described above.

In a fifth aspect, the invention relates to methods for the treatment and prevention of a disease, condition or disorder associated with leukotriene A4 hydrolase. The methods comprise administering to a mammal a therapeutically effective amount of a compound described above or a salt, hydrate or ester thereof. The disease or condition may be related to allergic, acute or chronic inflammation. The disease may be for example contact and atopic dermatitis, arthritis, allergic rhinitis, asthma or an autoimmune diseases such as Crohn's disease, psoriasis, ulcerative colitis, inflammatory bowel disease, multiple sclerosis, ankylosing spondylitis, and the like. Similarly, the compounds defined above can be used in preventing recurring inflammatory attacks. The compounds are also useful for treating and preventing atherosclerosis, thrombosis, stroke, acute coronary syndrome, stable angina, peripheral vascular disease, critical leg ischemia, intermittent claudication, abdominal aortic aneurysm and myocardial infarction.

Compounds of the invention, which inhibit tumor growth and metastases find utility in the treatment and prevention of cancer, including esophageal cancer, brain cancer, pancreatic cancer, and colon cancer.

These and other embodiments of the present invention will become apparent in conjunction with the description and claims that follow.

DETAILED DESCRIPTION OF THE INVENTION

Throughout this application, references are cited. The disclosure of each of these publications in its entirety is hereby incorporated by reference as if written herein.

Definitions

Throughout this specification the substituents are defined when introduced and retain their definitions.

Alkyl is intended to include linear, branched, or cyclic hydrocarbon structures and combinations thereof. Lower alkyl refers to alkyl groups of from 1 to 6 carbon atoms. Examples of lower alkyl groups include methyl, ethyl, propyl, isopropyl, butyl, s- and t-butyl and the like. Preferred alkyl groups are those of $C_{20}$ or below. Cycloalkyl is a subset of alkyl and includes cyclic hydrocarbon groups of from 3 to 8 carbon atoms. Examples of cycloalkyl groups include c-propyl, c-butyl, c-pentyl, norbornyl and the like.

$C_1$ to $C_{20}$ hydrocarbon includes alkyl, cycloalkyl, alkenyl, alkynyl, aryl, arylalkyl and combinations thereof. Examples include phenethyl, cyclohexylmethyl, camphoryl, adamantyl and naphthylethyl.

Alkoxy or alkoxyl refers to groups of from 1 to 8 carbon atoms of a straight, branched, cyclic configuration and combinations thereof attached to the parent structure through oxygen. Examples include methoxy, ethoxy, propoxy, isopropoxy, cyclopropyloxy, cyclohexyloxy and the like. Loweralkoxy refers to groups containing one to four carbons.

Alkoxyalkyl refers to ether groups of from 3 to 8 atoms of a straight, branched, cyclic configuration and combinations thereof attached to the parent structure through an alkyl. Examples include methoxymethyl, methoxyethyl, ethoxypropyl, and the like.

Alkoxyaryl refers to alkoxy substituents attached to an aryl, wherein the aryl is attached to the parent structure. Arylalkoxy refers to aryl substituents attached to an oxygen, wherein the oxygen is attached to the parent structure. Substituted arylalkoxy refers to a substituted aryl substituent attached to an oxygen, wherein the oxygen is attached to the parent structure.

Acyl refers to groups of from 1 to 8 carbon atoms of a straight, branched, cyclic configuration, saturated, unsaturated and aromatic and combinations thereof, attached to the parent structure through a carbonyl functionality. One or more carbons in the acyl residue may be replaced by nitrogen, oxygen or sulfur as long as the point of attachment to the parent remains at the carbonyl. Examples include acetyl, benzoyl, propionyl, isobutyryl, t-butoxycarbonyl, benzyloxycarbonyl and the like. Lower-acyl refers to groups containing one to four carbons.

Aryl and heteroaryl mean a 5- or 6-membered aromatic or heteroaromatic ring containing 0-3 heteroatoms selected from O, N, or S; a bicyclic 9- or 10-membered aromatic or heteroaromatic ring system containing 0-3 heteroatoms selected from O, N, or S; or a tricyclic 13- or 14-membered aromatic or heteroaromatic ring system containing 0-3 heteroatoms selected from O, N, or S. The aromatic 6- to 14-membered carbocyclic rings include, e.g., benzene and naphthalene, and according to the invention benzoxalane and residues in which one or more rings are aromatic, but not all need be. The 5- to 10-membered aromatic heterocyclic rings include, e.g., imidazole, pyridine, indole, thiophene, benzopyranone, thiazole, furan, benzimidazole, quinoline, isoquinoline, quinoxaline, pyrimidine, pyrazine, tetrazole and pyrazole.

Arylalkyl refers to a substituent in which an aryl residue is attached to the parent structure through alkyl. Examples are benzyl, phenethyl and the like. Heteroarylalkyl refers to a substituent in which a heteroaryl residue is attached to the parent structure through alkyl. Examples include, e.g., pyridinylmethyl, pyrimidinylethyl and the like. Heterocyclylalkyl refers to a substituent in which a heterocyclyl residue is attached to the parent structure through alkyl. Examples include morpholinoethyl and pyrrolidinylmethyl.

Heterocycle means a cycloalkyl or aryl residue in which from one to three carbons is replaced by a heteroatom selected from the group consisting of N, O and S. The nitrogen and sulfur heteroatoms may optionally be oxidized, and the nitrogen heteroatom may optionally be quaternized. Examples of heterocycles include pyrrolidine, pyrazole, pyrrole, indole, quinoline, isoquinoline, tetrahydroisoquinoline, benzofuran, benzodioxan, benzodioxole (commonly referred to as methylenedioxyphenyl, when occurring as a substituent), tetrazole, morpholine, thiazole, pyridine, pyridazine, pyrimidine, thiophene, furan, oxazole, oxazoline, isoxazole, dioxane, tetrahydrofuran and the like. It is to be noted that heteroaryl is a subset of heterocycle in which the heterocycle is aromatic. Examples of heterocyclyl residues additionally include piperazinyl, 2-oxopiperazinyl, 2-oxopiperidinyl, 2-oxo-pyrrolidinyl, 2-oxoazepinyl, azepinyl, 4-piperidinyl, pyrazolidinyl, imidazolyl, imidazolinyl, imidazolidinyl, pyrazinyl, oxazolidinyl, isoxazolidinyl, thiazolidinyl, isothiazolyl, quinuclidinyl, isothiazolidinyl, benzimidazolyl, thiadiazolyl, benzopyranyl, benzothiazolyl, tetrahydrofuryl, tetrahydropyranyl, thienyl, benzothienyl, thiamorpholinyl, thiamorpholinylsulfoxide, thiamorpholinylsulfone, oxadiazolyl, triazolyl and tetrahydroquinolinyl.

An oxygen heterocycle is a heterocycle containing at least one oxygen in the ring; it may contain additional oxygens, as well as other heteroatoms. A sulphur heterocycle is a heterocycle containing at least one sulphur in the ring; it may contain additional sulphurs, as well as other heteroatoms. A nitrogen heterocycle is a heterocycle containing at least one nitrogen in the ring; it may contain additional nitrogens, as well as other heteroatoms.

Oxygen heteroaryl is a subset of oxygen heterocycle; examples include furan and oxazole. Sulphur heteroaryl is a subset of sulphur heterocycle; examples include thiophene and thiazine. Nitrogen heteroaryl is a subset of nitrogen heterocycle; examples include pyrrole, pyridine and pyrazine.

A saturated nitrogenous heterocycle is a subset of nitrogen heterocycle. Saturated nitrogenous heterocycle contain at least one nitrogen and may contain additional nitrogens, as well as other heteroatoms. Examples include pyrrolidine, pyrazolidine, piperidine, morpholine, and thiomorpholine.

Substituted alkyl, aryl, cycloalkyl, heterocyclyl etc. refer to alkyl, aryl, cycloalkyl, or heterocyclyl wherein up to three H atoms in each residue are replaced with halogen, haloalkyl, hydroxy, loweralkoxy, carboxy, carboalkoxy (also referred to as alkoxycarbonyl), carboxamido (also referred to as alkylaminocarbonyl), cyano, carbonyl, nitro, amino, alkylamino, dialkylamino, mercapto, alkylthio, sulfoxide, sulfone, acylamino, amidino, phenyl, benzyl, heteroaryl, phenoxy, benzyloxy, or heteroaryloxy.

The terms "halogen" and "halo" refer to fluorine, chlorine, bromine or iodine.

The term "prodrug" refers to a compound that is made more active in vivo.

It will be recognized that the compounds of this invention can exist in radiolabeled form, i.e., the compounds may contain one or more atoms containing an atomic mass or mass number different from the atomic mass or mass number usually found in nature. Radioisotopes of hydrogen, carbon, phosphorous, fluorine, and chlorine include $^2H$, $^3H$, $^{13}C$, $^{14}C$, $^{15}N$, $^{35}S$, $^{18}F$, and $^{36}Cl$, respectively. Compounds that contain those radioisotopes and/or other radioisotopes of other atoms are within the scope of this invention. Tritiated, i.e. $^3H$, and carbon-14, i.e., $^{14}C$, radioisotopes are particularly preferred for their ease in preparation and detectability. Radiolabeled compounds of formula Ψ of this invention and prodrugs thereof can generally be prepared by methods well known to those skilled in the art. Conveniently, such radiolabeled compounds can be prepared by carrying out the procedures disclosed in the Examples and Schemes by substituting a readily available radiolabeled reagent for a non-radiolabeled reagent.

As used herein, and as would be understood by the person of skill in the art, the recitation of "a compound" is intended to include salts, solvates, co-crystals and inclusion complexes of that compound.

The term "solvate" refers to a compound in the solid state, wherein molecules of a suitable solvent are incorporated in the crystal lattice. A suitable solvent for therapeutic administration is physiologically tolerable at the dosage administered. Examples of suitable solvents for therapeutic administration are ethanol and water. When water is the solvent, the solvate is referred to as a hydrate. In general, solvates are formed by dissolving the compound in the appropriate solvent and isolating the solvate by cooling or using an antisolvent. The solvate is typically dried or azeotroped under ambient conditions. Co-crystals are combinations of two or more distinct molecules arranged to create a unique crystal form whose physical properties are different from those of its pure constituents. Pharmaceutical co-crystals have recently become of considerable interest for improving the solubility, formulation and bioavailability of such drugs as itraconazole [see Remenar et al. J. Am. Chem. Soc. 125, 8456-8457 (2003)] and fluoxetine. Inclusion complexes are described in Remington: The Science and Practice of Pharmacy 19$^{th}$ Ed. (1995) volume 1, page 176-177. The most commonly employed inclusion complexes are those with cyclodextrins, and all cyclodextrin complexes, natural and synthetic, with or without added additives and polymer(s), as described in U.S. Pat. Nos. 5,324,718 and 5,472,954, are specifically encompassed within the claims. The disclosures of Remington and the '718 and '954 patents are incorporated herein by reference.

The compounds described herein may contain asymmetric centers and may thus give rise to enantiomers, diastereomers, and other stereoisomeric forms. Each chiral center may be defined, in terms of absolute stereochemistry, as (R)— or (S)—. The present invention is meant to include all such possible isomers, as well as, their racemic and optically pure forms. Optically active (R)— and (S)— isomers may be prepared using chiral synthons or chiral reagents, or resolved using conventional techniques. The prefix "rac" refers to a racemate. When the compounds described herein contain olefinic double bonds or other centers of geometric asymmetry, and unless specified otherwise, it is intended that the compounds include both E and Z geometric isomers. The representation of the configuration of any carbon-carbon double bond appearing herein is selected for convenience only, and unless explicitly stated, is not intended to designate a particular configuration. Thus a carbon-carbon double bond depicted arbitrarily as E may be Z E, or a mixture of the two in any proportion. Likewise, all tautomeric forms are also intended to be included.

The graphic representations of racemic, ambiscalemic and scalemic or enantiomerically pure compounds used herein are taken from Maehr J. Chem. Ed. 62, 114-120 (1985): solid and broken wedges are used to denote the absolute configuration of a chiral element; wavy lines and single thin lines indicate disavowal of any stereochemical implication which the bond it represents could generate; solid and broken bold lines are geometric descriptors indicating the relative configuration shown but denoting racemic character; and wedge outlines and dotted or broken lines denote enantiomerically pure compounds of indeterminate absolute configuration.

Terminology related to "protecting", "deprotecting" and "protected" functionalities occurs throughout this application. Such terminology is well understood by persons of skill in the art and is used in the context of processes that involve sequential treatment with a series of reagents. In that context, a protecting group refers to a group, which is used to mask a functionality during a process step in which it would otherwise react, but in which reaction is undesirable. The protecting group prevents reaction at that step, but may be subsequently removed to expose the original functionality. The removal or "deprotection" occurs after the completion of the reaction or reactions in which the functionality would interfere. Thus, when a sequence of reagents is specified, as it is in the processes of the invention, the person of ordinary skill can readily envision those groups that would be suitable as "protecting groups". Suitable groups for that purpose are discussed in standard textbooks in the field of chemistry, such as Protective Groups in Organic Synthesis by T. W. Greene [John Wiley & Sons, New York, 1991], which is incorporated herein by reference.

A comprehensive list of abbreviations utilized by organic chemists appears in the first issue of each volume of the Journal of Organic Chemistry. The list, which is typically presented in a table entitled "Standard List of Abbreviations", is incorporated herein by reference.

In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants that are in themselves known, but are not mentioned here. The starting materials, are either commercially available, synthesized as described in the examples or may be obtained by the methods well known to persons of skill in the art.

LTA4H inhibitors have been shown to be effective anti-inflammatory agents in pre-clinical studies. For example, oral administration of LTA4H inhibitor SC57461 to rodents resulted in the inhibition of ionophore-induced LTB4 production in mouse blood ex vivo, and in rat peritoneum in vivo (Kachur et al., 2002, J. Pharm. Exp. Ther. 300(2), 583-587). Furthermore, eight weeks of treatment with the same inhibitor compound significantly improved colitis symptoms in a primate model (Penning, 2001, Curr. Pharm. Des. 7(3): 163-179). The spontaneous colitis that develops in these animals is very similar to human IBD. Therefore persons of skill in the art accept that positive results in LTA4H models are predictive of therapeutic utility in this and other human inflammatory diseases.

The inflammatory response is characterized by pain, increased temperature, redness, swelling, or reduced function, or by a combination of two or more of these symptoms. The terms inflammation, inflammatory diseases or inflammation-mediated diseases or conditions include, but are not limited to, acute inflammation, allergic inflammation, and chronic inflammation.

Autoimmune diseases are associated with chronic inflammation. There are about 75 different autoimmune disorders known that may be classified into two types, organ-specific (directed mainly at one organ) and non-organ-specific (affecting multiple organs).

Examples of organ-specific autoimmune disorders are insulin-dependent diabetes (Type I) which affects the pancreas, Hashimoto's thyroiditis and Graves' disease which affect the thyroid gland, pernicious anemia which affects the stomach, Cushing's disease and Addison's disease which affect the adrenal glands, chronic active hepatitis which affects the liver; polycystic ovary syndrome (PCOS), celiac disease, psoriasis, inflammatory bowel disease (IBD) and ankylosing spondylitis.

Examples of non-organ-specific autoimmune disorders are rheumatoid arthritis, multiple sclerosis, systemic lupus and myasthenia gravis.

Furthermore, the compounds, compositions and methods of the present invention are useful in treating cancer. Leukotriene synthesis has been shown to be associated with different types of cancer including esophageal cancer, brain cancer, pancreatic cancer, colon cancer.

The terms "methods of treating or preventing" mean amelioration, prevention or relief from the symptoms and/or effects associated with lipid disorders. The term "preventing" as used herein refers to administering a medicament beforehand to forestall or obtund an acute episode. The person of ordinary skill in the medical art (to which the present method claims are directed) recognizes that the term "prevent" is not an absolute term. In the medical art it is understood to refer to the prophylactic administration of a drug to substantially diminish the likelihood or seriousness of a condition, and this is the sense intended in applicants' claims. As used herein, reference to "treatment" of a patient is intended to include prophylaxis. Throughout this application, various references are referred to. The disclosures of these publications in their entireties are hereby incorporated by reference as if written herein.

The term "mammal" is used in its dictionary sense. Humans are included in the group of mammals, and humans would be the preferred subjects of the methods.

While it may be possible for the compounds to be administered as the raw chemical, it is preferable to present them as a pharmaceutical composition. According to a further aspect, the present invention provides a pharmaceutical composition comprising a compound of formula I, II, III, or IV or a pharmaceutically acceptable salt or solvate thereof, together with one or more pharmaceutical carriers thereof and optionally one or more other therapeutic ingredients. The carrier(s) must be "acceptable" in the sense of being compatible with the other ingredients of the formulation and not deleterious to the recipient thereof.

The formulations include those suitable for oral, parenteral (including subcutaneous, intradermal, intramuscular, intravenous and intraarticular), rectal and topical (including dermal, buccal, sublingual and intraocular) administration. The most suitable route may depend upon the condition and disorder of the recipient. The formulations may conveniently be presented in unit dosage form and may be prepared by any of the methods well known in the art of pharmacy. All methods include the step of bringing into association a compound of formula I, II, III, or IV or a pharmaceutically acceptable salt or solvate thereof ("active ingredient") with the carrier, which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets each containing a predetermined amount of the active ingredient; as a powder (including micronized and nanoparticulate powders) or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Molded tablets may be made by molding in a suitable machine a mixture of the powdered compound moistened with an inert liquid diluent. The tablets may optionally be coated or scored and may be formulated so as to provide sustained, delayed or controlled release of the active ingredient therein.

The pharmaceutical compositions may include a "pharmaceutically acceptable inert carrier", and this expression is intended to include one or more inert excipients, which include starches, polyols, granulating agents, microcrystalline cellulose, diluents, lubricants, binders, disintegrating agents, and the like. If desired, tablet dosages of the disclosed compositions may be coated by standard aqueous or non-aqueous techniques, "Pharmaceutically acceptable carrier" also encompasses controlled release means.

Compositions of the present invention may also optionally include other therapeutic ingredients, anti-caking agents, preservatives, sweetening agents, colorants, flavors, desiccants, plasticizers, dyes, and the like. Any such optional ingredient must, of course, be compatible with the compound of the invention to insure the stability of the formulation. The dose range for adult humans is generally from 0.1 μg to 10 g/day orally. Tablets or other forms of presentation provided in discrete units may conveniently contain an amount of compound of the invention which is effective at such dosage or as a multiple of the same, for instance, units containing 0.1 mg to 500 mg, usually around 5 mg to 200 mg. The precise amount of compound administered to a patient will be the responsibility of the attendant physician. However, the dose employed will depend on a number of factors, including the age and sex of the patient, the precise disorder being treated, and its severity. The frequency of administration will depend on the pharmacodynamics of the individual compound and the formulation of the dosage form, which may be optimized by methods well known in the art (e.g. controlled or extended release tablets, enteric coating etc.).

Combination therapy can be achieved by administering two or more agents, each of which is formulated and administered separately, or by administering two or more agents in a single formulation. Other combinations are also encompassed by combination therapy. For example, two agents can be formulated together and administered in conjunction with a separate formulation containing a third agent. While the two or more agents in the combination therapy can be administered simultaneously, they need not be. For example, administration of a first agent (or combination of agents) can precede administration of a second agent (or combination of agents) by minutes, hours, days, or weeks. Thus, the two or more agents can be administered within minutes of each other or within any number of hours of each other or within any number or days or weeks of each other. In some cases even longer intervals are possible.

While in many cases it is desirable that the two or more agents used in a combination therapy be present in within the patient's body at the same time, this need not be so. Combination therapy can also include two or more administrations of one or more of the agents used in the combination. For example, if agent X and agent Y are used in a combination, one could administer them sequentially in any combination one or more times, e.g., in the order X-Y-X, X-X-Y, Y-X-Y, Y-Y-X, X-X-Y-Y, etc.

As LTA4H inhibitors, the compounds of formula I, II, III, or IV have utility in treating and preventing inter alia inflammation. The compounds and compositions can be used advantageously in combination with other agents useful in treating and preventing inflammatory conditions and for treating and preventing atherosclerosis, thrombosis, stroke, acute coronary syndrome, stable angina, peripheral vascular disease, critical leg ischemia, intermittent claudication, abdominal aortic aneurysm and myocardial infarction.

The present invention relates to compounds exhibiting LTA4H enzyme inhibition, having the general formula III

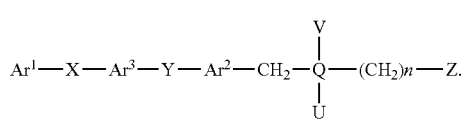

III

The present invention also relates to compounds exhibiting LTA4H enzyme inhibition, having the general formula IV

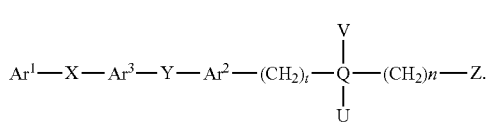

IV

One aspect of the invention relates to 3-(triaryl)-2-aminopropanol derivative inhibitors of LTA4H inhibitors, having the general formula I

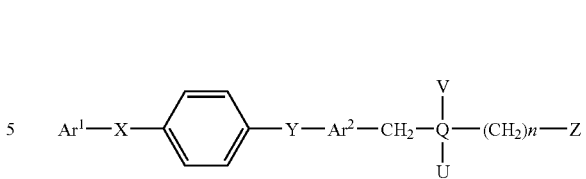

I

For instance, the following are examples of compounds of general formula I:

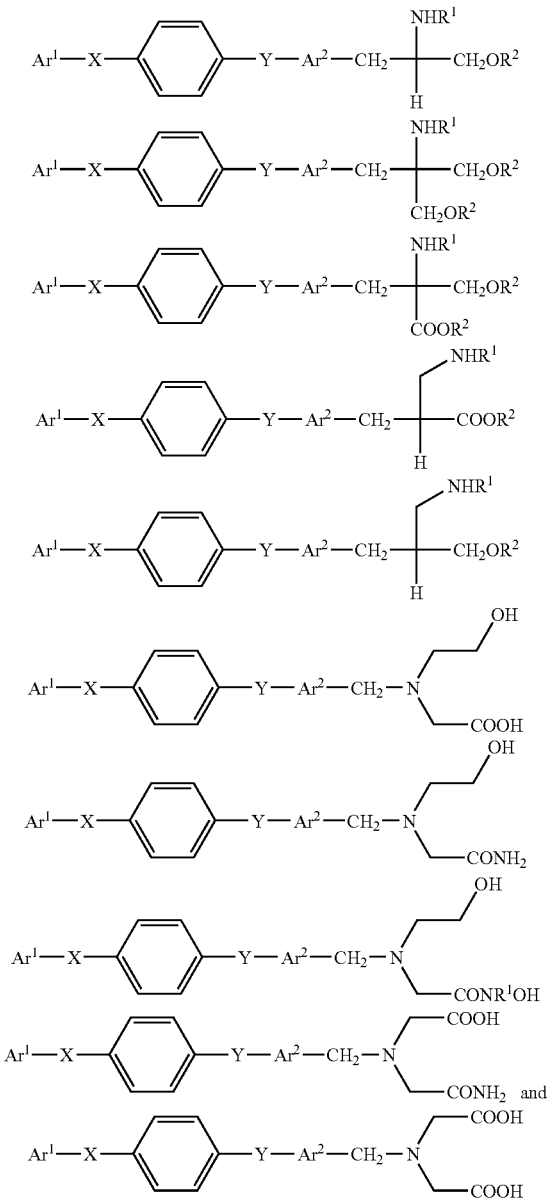

In one embodiment, $Ar^1$ and $Ar^2$ of formula II are chosen independently from phenyl and phenyl substituted with from one to three substituents chosen independently from halogen, haloalkyl, hydroxy, loweralkoxy, carboxy, alkoxycarbonyl, aminocarbonyl, cyano, carbonyl, nitro, amino, alkylamino, dialkylamino, mercapto, alkylthio, alkyl sulfoxide, alkyl sulfone and acylamino. In another embodiment $Ar^1$ and $Ar^2$ of formula II are phenyl. In a third embodiment $R^1$ of formula II is hydrogen. In a fourth embodiment Y of formula II is —O—. In a fifth embodiment X of formula II is chosen from —O—, —CH₂— and —C(=O)—. In a further embodiment Z of formula II is chosen from —COOH, —COOCH₃, —CONH₂, —OH, —OCH₃ and —NH₂. In a preferred embodiment regarding formula II, Ar¹ and Ar² are phenyl, R¹ is hydrogen, Y is —O—, and Z is chosen from —COOH, —COOCH₃, —CONH₂, —OH, —OCH₃ and —NH₂.

In another aspect the present invention provides a pharmaceutical composition comprising a pharmaceutically acceptable carrier and a therapeutically effective amount of at least one compound as described above.

Methods of the invention parallel the compositions and formulations. The methods comprise administering to a patient in need of treatment a therapeutically effective amount of a compound according to the invention.

The present invention provides a method for inhibiting leukotriene A4 hydrolase comprising contacting the LTA4H enzyme with a therapeutically effective amount of a compound or a salt, hydrate or ester thereof according to formulas I, II, III, and IV.

Furthermore, the present invention provides a method for inhibiting a disorder associated with leukotriene A4 hydrolase comprising administering to a mammal a therapeutically effective amount of a compound or a salt, hydrate or ester thereof. All of the compounds falling within the foregoing parent genus and its subgenera are useful as LTA4H inhibitors. It may be found upon examination that additional species and genera not presently excluded are not patentable to the inventors in this application. In this case, the exclusion of species and genera in applicants' claims are to be considered artifacts of patent prosecution and not reflective of the inventors' concept or description of their invention. The invention, in a composition aspect, is all compounds of formula I, II, III, and IV except those that are in the public's possession.

In some embodiments the disorder is associated with inflammation. In some embodiments the disorder is selected from allergic inflammation, acute inflammation and chronic inflammation.

Compounds of the genus represented by formula I, II, III, or IV above are inhibitors of LTA₄H enzyme. As such they have utility in treating and preventing inflammatory diseases and disorders, as described above, particularly for such conditions as asthma, chronic obstructed pulmonary disease (COPD), rheumatoid arthritis, multiple sclerosis, inflammatory bowel diseases (IBD); including Crohn's disease and ulcerative colitis, or psoriasis, which are each characterized by excessive or prolonged inflammation at some stage of the disease.

Recent research indicates that the compounds are also useful for treating and preventing atherosclerosis, thrombosis, stroke, acute coronary syndrome, stable angina, peripheral vascular disease, critical leg ischemia, intermittent claudication, abdominal aortic aneurysm and myocardial infarction.

The compounds may be presented as salts. The term "pharmaceutically acceptable salt" refers to salts whose counter ion derives from pharmaceutically acceptable non-toxic acids and bases. Suitable pharmaceutically acceptable base addition salts for the compounds of the present invention include, but are not limited to, metallic salts made from aluminum, calcium, lithium, magnesium, potassium, sodium and zinc or organic salts made from lysine, N,N-dialkyl amino acid derivatives (e.g. N,N-dimethylglycine, piperidine-1-acetic acid and morpholine-4-acetic acid), N,N'-dibenzylethylenediamine, chloroprocaine, choline, diethanolamine, ethylenediamine, meglumine (N-methylglucamine) and procaine. When the compounds contain a basic residue, suitable pharmaceutically acceptable base addition salts for the compounds of the present invention include inorganic acids and organic acids. Examples include acetate, benzenesulfonate (besylate), benzoate, bicarbonate, bisulfate, carbonate, camphorsulfonate, citrate, ethanesulfonate, fumarate, gluconate, glutamate, bromide, chloride, isethionate, lactate, maleate, malate, mandelate, methanesulfonate, mucate, nitrate, pamoate, pantothenate, phosphate, succinate, sulfate, tartrate, p-toluenesulfonate, and the like.

In general, the compounds of the present invention may be prepared by the methods illustrated in the general reaction schemes as, for example, described below, or by modifications thereof, using readily available starting materials, reagents and conventional synthesis procedures. The following specific non-limiting examples are illustrative of the invention.

See examples below.

EXAMPLES

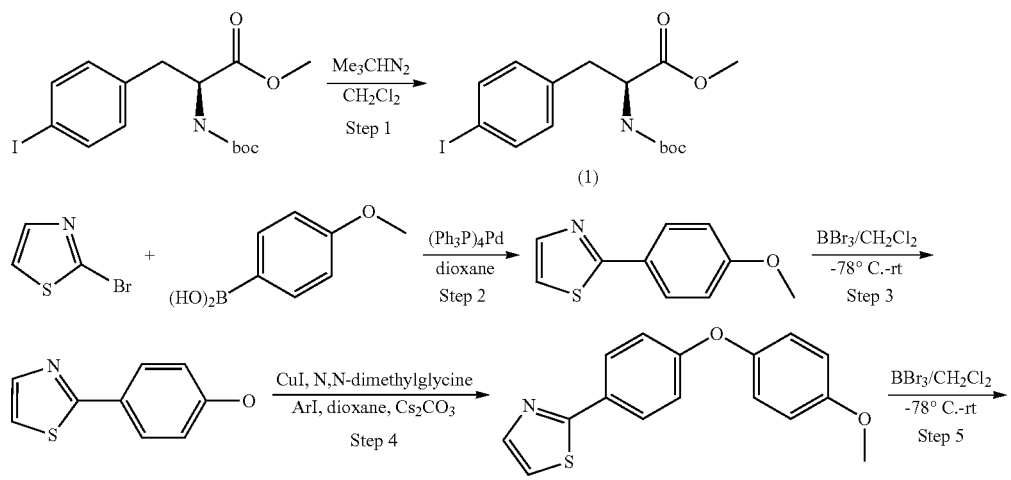

Scheme I

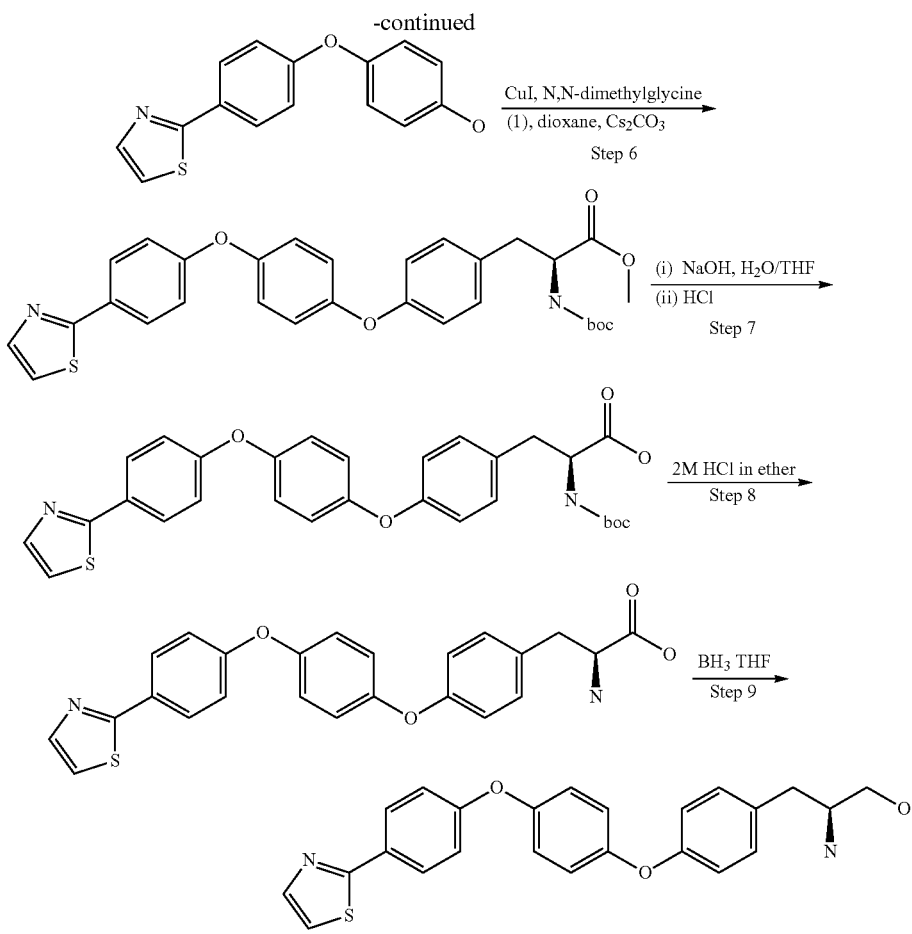
Scheme II
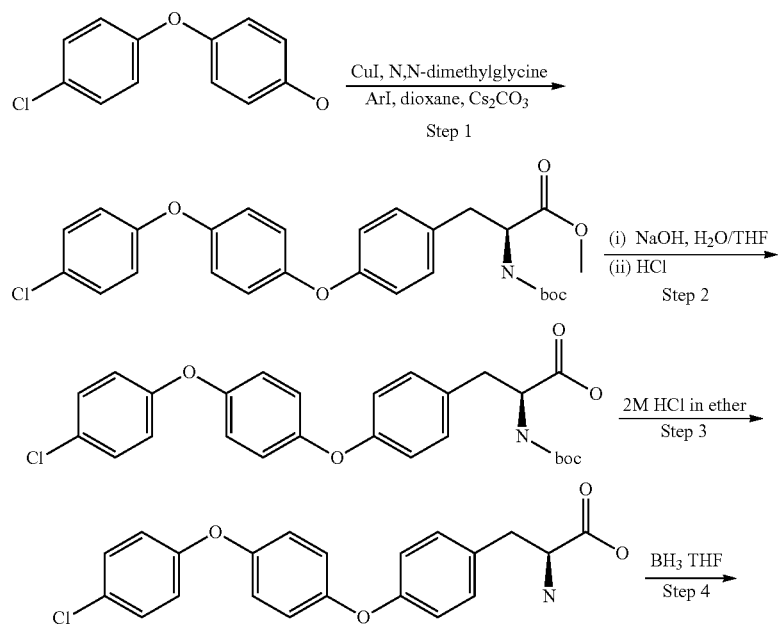

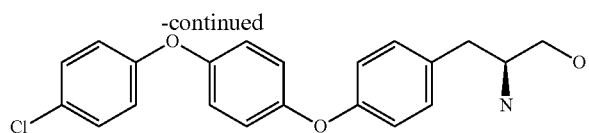
Scheme III
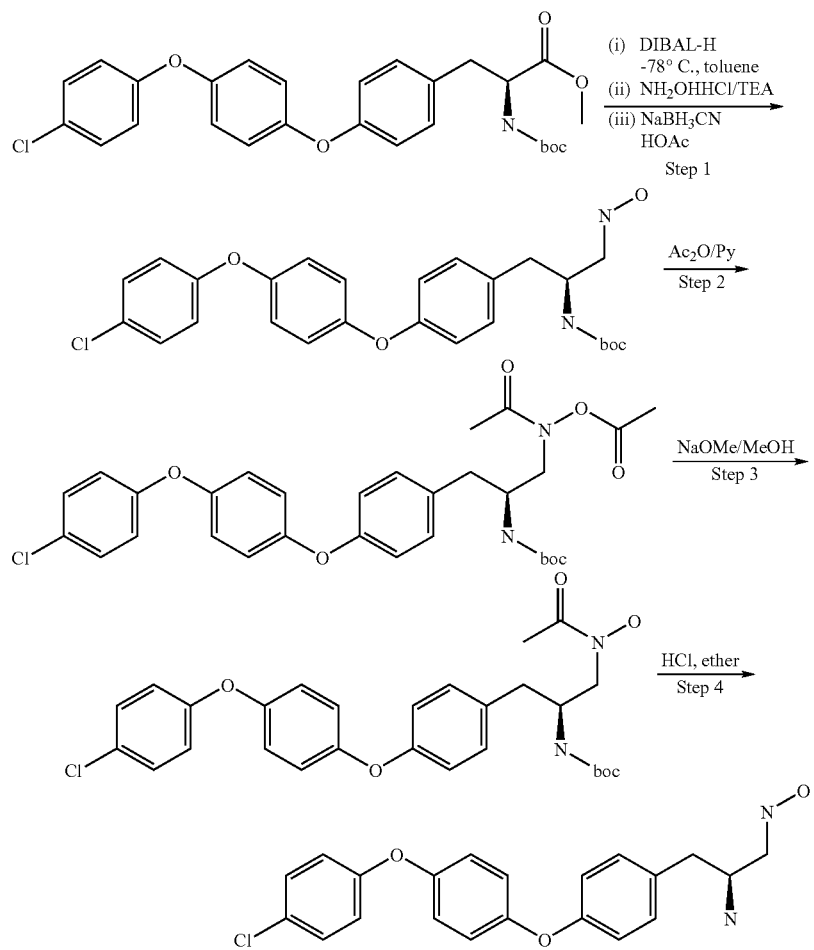
Scheme IV
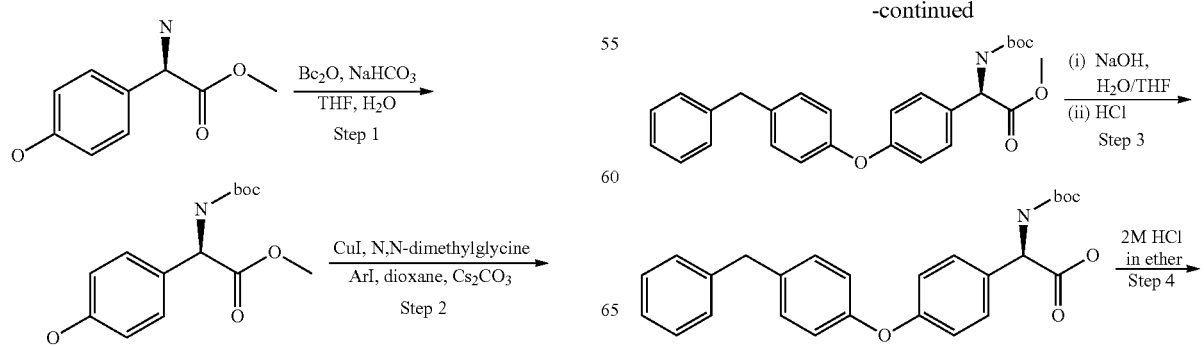

-continued

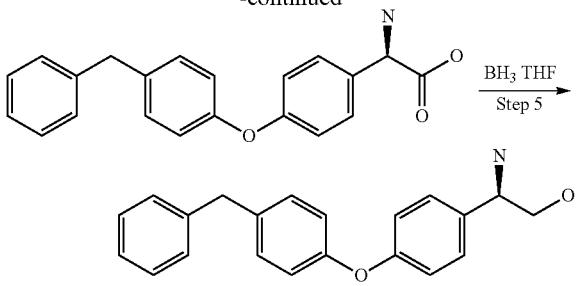

Scheme V

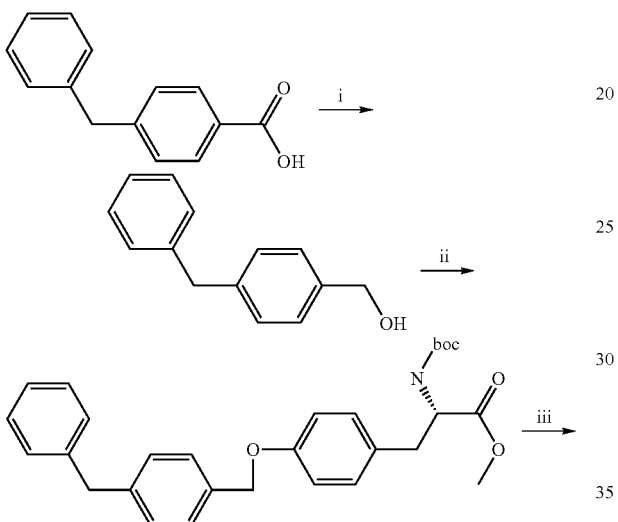

Example 1

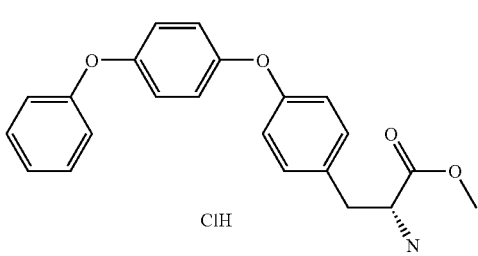

Step 1:

(R)-2-tert-Butoxycarbonylamino-3-[4-(4-phenoxy-phenoxy)-phenyl]-propionic acid methyl ester To a solution of Boc-D-Tyrosine-Methyl ester (0.150 g, 0.508 mmol), 4-Phenoxyphenyl-boronic acid (0.109 g, 0.508 mmol), and triethylamine (0.355 mL, 2.539 mmol) in anhydrous dichloromethane (DCM) (12.5 mL) at room temperature under an atmosphere of nitrogen was added copper (II) acetate (0.070 g, 0.508 mmol), and the resulting mixture was stirred at room temperature for about 18 h. The reaction mixture was washed with 20 mL of water and 20 mL of DCM and filtered. The DCM layer was then extracted. The aqueous layer was re-extracted with DCM (2×15 mL). The combined organic layers were dried over anhydrous $Na_2SO_4$, filtered, and the solvent was removed in vacuo to obtain the crude mixture, which was purified by of silica gel flash chromatography, using ethyl acetate (EtOAc)/hexane (gradient system), to obtain the product (110 mg, 47%): $^1$H NMR (400 MHz, $CDCL_3$): δ 1.42 (s, 9H), 2.98-3.09 (m, 2H), 3.71 (d, J=5.2 Hz), 4.55-4.58 (m, 1H), 4.98-5.01 (m, 1H), 6.75 (d, 1H, J=8.4 Hz), 6.91-7.02 (m, 6H), 7.07-7.11 (m, 3H), 7.31-7.35 (m, 2H); MS: m/z 364 (MH)$^+$ & no -boc group, m/z 464 (MH)$^+$.

Step 2:

(R)-2-Amino-3-[4-(4-phenoxy-phenoxy)-phenyl]-propionic acid methyl ester hydrochloride A solution of the product (0.110 g, 0.221 mmol) in step 1 in 4N HCl in dioxane (1.1 mL, 4.4 mmol) and methanol (1.05 mL) was stirred at ambient temperature for about 2 hours and then concentrated in vacuo. The residue was triturated with diethyl ether to afford the desired product as a white solid (0.060 g, 68%): $^1$H NMR (400 MHz, $CDCL_3$): δ 3.11-3.27 (m, 2H), 3.82 (d, 3H, J=5.2 Hz), 4.21-4.32 (m, 1H), 6.78 (d, 1H, J=8.4 Hz), 6.96-6.99 (m, 3H), 7.01 (d, 3H, J=0.4 Hz), 7.05-7.11 (m, 2H), 7.23 (d, 2H, J=8.8 Hz), 7.34 (t, 2H, J=8.0 Hz); m/z 380 (MH)$^+$; LCMS (UV) 89.8%.

Example 2

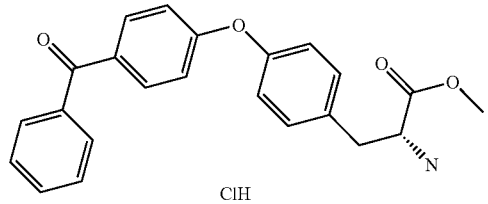

Step 1:

(R)-3-[4-(4-Benzoyl-phenoxy)-phenyl]-2-tert-butoxycarbonylamino-propionic acid methyl ester To a solution of N,N-Dimethylformamide (DMF) (3.16 mL) and potassium carbonate (0.222 g, 1.605 mmol) was added Boc-D-Tyrosine-Methyl ester (0.158 g, 0.535 mmol) and 4-Fluorobenzophenone (0.160 g, 0.802 mmol) at 100° C. under an atmosphere of nitrogen for 42 hours. The mixture was poured into 30 mL water solution and extracted with ethyl acetate (EtOAc) (4×10 mL). The combined organic layers were washed with brine (40 mL) and dried over anhydrous $Na_2SO_4$. The organic layer was concentrated in vacuo to obtain the crude mixture, which was purified by of silica gel flash chromatography, using EtOAc/hexane (gradient system), to obtain the product (0.060 g, 24%): $^1$H NMR (400 MHz, $CDCL_3$): δ 1.42 (s, 9H), 2.99-3.17 (m, 2H), 3.71-3.74 (m, 3H), 4.53-4.61 (m, 1H), 4.96-5.16 (m, 1H), 6.75 (d, 1H, J=8.4 Hz), 6.97-7.03 (m, 4H), 7.16 (d, 2H, J=8.4 Hz), 7.46-7.50 (m, 2H), 7.56-7.58 (m, 1H), 7.77-7.83 (m, 3H).

Step 2:

(R)-2-Amino-3-[4-(4-benzoyl-phenoxy)-phenyl]-propionic acid methyl ester hydrochloride A solution of the product (0.050 g, 0.105 mmol) in step 1 in 4.0M HCl in diethyl ether (0.52 mL, 2.103 mmol) and methanol (0.5 mL), was stirred at ambient temperature for about 2 hours and then concentrated in vacuo. The residue was triturated with ether and dried in a 55° C. vacuum oven for one hour to afford the desired product as a white solid (0.020 g, 46%): $^1$H NMR (400 MHz, DMSO): δ 3.17 (t, 2H, J=6.8 Hz), 3.68-3.71 (m, 4H) 4.30 (t, 1H, J=6.4 Hz), 6.72 (d, 1H, J=8.4 Hz), 7.00 (d, 1H, J=8.4 Hz), 7.09-7.14 (m, 4H), 7.34 (d, 2H, J=8.4 Hz), 7.55-7.58 (m, 2H), 7.72 (d, 2H, J=* Hz), 7.79 (d, 2H, J=9.2 Hz); m/z 376 (MH)$^+$; LCMS (UV) 85%.

Example 3

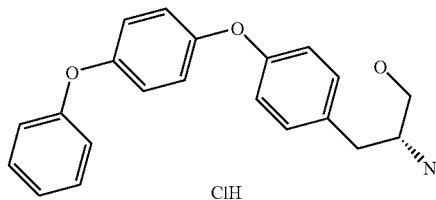

Step 1:

(R)-2-tert-Butoxycarbonylamino-3-[4-(4-phenoxy-phenoxy)-phenyl]-propionic acid methyl ester To a solution of Boc-D-Tyrosine-Methyl ester (0.950 g, 3.217 mmol), 4-Phenoxyphenyl-boronic acid (0.688 g, 3.217 mmol), and triethylamine (228 mL, 16.083 mmol) in anhydrous dichloromethane (DCM) (79.2 mL) at room temperature under an atmosphere of nitrogen was added copper (II) acetate (0.445 g, 3.217 mmol), and the resulting mixture was stirred at room temperature for about 42 hours. The reaction mixture was washed with 60 mL of water and 20 mL of DCM and filtered. The DCM layer was then extracted. The aqueous layer was re-extracted with DCM (2×30 mL). The organic layers were combined, washed with 60 mL of brine, and seperated. Organic layer was dried over anhydrous Na$_2$SO$_4$, filtered, and the solvent was removed in vacuo to obtain the crude mixture, which was purified by silica gel flash chromatography, using EtOAc/hexane (gradient system), to obtain the product (0.57 g, 50%): $^1$H NMR (400 MHz, CDCl$_3$): δ 1.42 (s, 9H), 1.59 (s, 1H), 2.99-3.11 (m, 2H), 3.67-3.73 (m, 3H), 4.57 (d, 1H, J=7.2 Hz), 4.99 (d, 1H, J=8 Hz), 6.92 (d, 2H, J=8.8 Hz), 6.99-7.01 (m, 5H), 7.07-7.10 (m, 3H), 7.31-7.35 (m, 2H).

Step 2:

{(R)-1-Hydroxymethyl-2-[4-(4-phenoxy-phenoxy)-phenyl]-ethyl}-carbamic acid tert-butyl ester To a solution of ethanol/tetrahydrofuran (50/50) (2.16 mL), (R)-2-tert-Butoxycarbonylamino-3-[4-(4-phenoxyphenoxy)-phenyl]-propionic acid methyl ester (0.125 g, 0.324 mmol) was added. Then lithium chloride (0.046 g, 1.296 mmol) and sodium borohydride (0.041 g, 1.296 mmol) dissolved in ethanol/tetrahydrofuran (50/50) (2.16 mL) were added to the reaction mixture. The resulting mixture was stirred starting at 0° C. and warming to room temperature over 18 hours. Reaction was stopped with 1N HCl (1.0 mL) and then extracted with EtOAc (20 mL) and water (15 mL). The organic layer was separated. Organic layer was washed with each and separated for the next wash, 1N HCl (15 mL), sodium bicarbonate (15 mL), and brine (15 mL). The organic layer was then dried over Na$_2$SO$_4$, filtered, and concentrated in vacuo to obtain a crude mixture, which was purified by silica gel flash chromatography, using EtOAc/hexane (gradient system), to obtain the product (0.1 g, 71%): $^1$H NMR (400 MHz, CDCl$_3$): δ 1.42 (s, 9H), 2.75-2.82 (m, 2H), 3.56-3.70 (m, 2H), 3.85 (s, 1H), 4.73 (s, 1H), 6.94 (d, 2H, J=8.8 Hz), 6.99-7.01 (m, 5H), 7.08 (t, 1H, J=7.2 Hz), 7.17 (d, 2H, J=8.8 Hz), 7.31-7.35 (m, 2H).

Step 3:

(R)-2-Amino-3-[4-(4-phenoxy-phenoxy)-phenyl]-propan-1-ol hydrochloride

A solution of the product (0.10 g, 0.23 mmol) in step 1 in 4N HCl in dioxane (1.15 mL, 4.6 mmol) and methanol (1.00 mL) was stirred at ambient temperature for about 2 hours and then concentrated in vacuo. The residue was triturated with diethyl ether to afford the desired product as a white solid (0.090 g, 64%): $^1$H NMR (400 MHz, CD$_3$OD): 2.90-2.93 (m, 2H), 3.42-3.56 (m, 2), 3.69-3.73 (m, 1H), 6.95-7.01 (m, 7H), 7.07-7.09 (m, 2H), 7.26 (d, 2H, J=6.8 Hz), 7.31-7.36 (m, 2H); m/z 336 (MH)$^+$; LCMS (UV) 100%.

Example 4

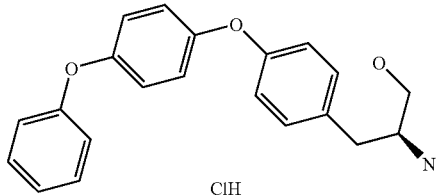

Step 1:

(S)-4-(4-Hydroxy-benzyl)-2,2-dimethyl-oxazolidine-3-carboxylic acid tert-butyl ester A solution of Boc-L-Tyrosinol (1 g, 3.74 mmol), p-toluenesulfonic acid (0.0356 g, 0.187 mmol), and dichloromethane (DCM) (7.66 mL) was added 2,2 dimethoxypropane (2.3 mL, 18.7 mmol). The resulting mixture was stirred overnight at room temperature under nitrogen. Reaction mixture was washed with sodium bicarbonate (20 mL). Organic layer was separated and washed with sodium bicarbonate (20 mL). The sodium bicarbonate layers were combined and washed with DCM (20 mL). DCM layers were combined, dried over MgSO$_4$, filtered, and concentrated in vacuo to obtain a crude mixture that was purified by silica gel flash chromatography, using EtOAc/hexane (gradient system) to obtain product (0.87 g, 83%): $^1$H NMR (400 MHz, CDCl$_3$): δ 1.42-1.68 (m, 15H), 2.57-2.63 (m, 1H), 3.00-3.14 (m, 1H), 3.74-3.80 (m, 2H), 3.91-4.05 (m, 1H), 6.77 (t, 2H, J=8.8 Hz), 7.08 (dd, 1H, J=8.0 Hz, J=16 Hz).

Step 2:

(S)-2,2-Dimethyl-4-[4-(4-phenoxy-phenoxy)-benzyl]-oxazolidine 3-carboxylic acid tert-butyl ester To a solution of (S)-4-(Hydroxy-benzyl)-2,2-dimethyl-oxazolidine-3-carboxylic acid tert-butyl ester (0.250 g, 0.846 mmol), 4-Phenoxyphenyl-boronic acid (0.181 g, 0.846 mmol), and triethylamine (0.59 mL, 4.232 mmol) in anhydrous dichloromethane (DCM) (20.8 mL) at room temperature under an atmosphere of nitrogen was added copper (II) acetate (0.154 g, 0.846 mmol), and the resulting mixture was stirred at room temperature for about 60 hours. The reaction mixture was washed with 20 mL of water and 20 mL of DCM and filtered. The DCM layer was then extracted. The aqueous layer was re-extracted with DCM (2×15 mL). The combined organic layers were dried over anhydrous $Na_2SO_4$, filtered, and the solvent was removed in vacuo to obtain the crude mixture, which was purified by of silica gel flash chromatography, using EtOAc/hexane (gradient system), to obtain the product (0.030 g, 8%).

Step 3:

(S)-2-Amino-3-[4-(4-phenoxy-phenoxy)-phenyl]-propan-1-ol hydrochloride

A solution of the product (0.030 g, 0.0631 mmol) in step 2 in 4N HCl in dioxane (0.315 mL, 1.26 mmol) and methanol (0.3 mL) was stirred at ambient temperature for about 2 hours and then concentrated in vacuo. The residue was triturated with diethyl ether to afford the desired product as a white solid (0.020 g, 87%): $^1$H NMR (400 MHz, $CD_3OD$): 2.910 (t, 2H, J=8 Hz), 3.412-3.478 (m, 1H), 3.51-3.55 (m, 1H), 3.70 (dd, 1H, J=3.6 Hz, J=11.6 Hz), 6.59-6.99 (m, 4H), 7.00 (s, 3H), 7.09-7.11 (m, 1H), 7.26 (d, 2H, J=8.8 Hz), 7.32-7.36 (m, 2H); m/z 336 $(MH)^+$; LCMS (UV) 94%.

Example 5

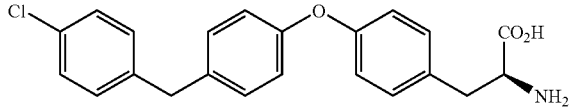

Step 1:

(S)-2-tert-Butoxycarbonylamino-3-(4-iodo-phenyl)-propionic acid methyl ester

To a clear, colorless solution of (S)-3-tert-Butoxycarbonylamino-4-(4-iodo-phenyl)-propionic acid (3.00 g, 7.67 mmol) in a solution of benzene (18 mL) and methanol (15 mL) at ambient temperature under a nitrogen atmosphere was added 2.0 M solution of (trimethylsilyl)diazomethane in diethyl ether until the reaction solution remained yellow, which required 5 mL (10.0 mmol). The solution was concentrated in vacuo to give the ester as a white solid (2.96 g, 95% yield): $^1$H NMR ($CDCl_3$): δ 7.61 (d, 2H, J=8.4 Hz), 6.87 (br d, 2H, J=8.4 Hz), 4.97 (br d, 1H, J=7.2 Hz), 4.56 (br d, 1H, J=8.0 Hz), 3.72 (s, 3H), 3.02 (dq, 2H, J=13.6 Hz, J=5.6 Hz), 1.42 (s, 9H).

Step 2:

(S)-2-tert-Butoxycarbonylamino-3-{4-[4-(4-chloro-benzyl)-phenoxy]-phenyl}-propionic acid methyl ester To a mixture of the product (2.96 g, 7.30 mmol) in step 1,4-(4-chlorobenzyl)phenol (1.60 g, 7.30 mmol), N,N-dimethylglycine (0.753 g, 7.30 mmol), and cesium carbonate (7.14 g, 21.9 mmol) in 1,4-dioxane at ambient temperature under an atmosphere of nitrogen was added copper (1) iodide (0.695 g, 3.65 mmol) in one portion. The reaction vial was sealed and heated at 100° C. for 20 h. The mixture was cooled to ambient temperature and diluted with a solution of $H_2O$ (30 mL) and brine (60 mL). After extracting with EtOAc (3×30 mL), the organic layer was washed with $H_2O$ (30 mL) and brine (30 mL), dried over sodium sulfate, and concentrate in vacuo to a black liquid (2.67 g). The crude oil was purified by silica gel flash chromatography to obtain the ester as a clear, yellow oil (1.34 g, 37%): $^1$H NMR ($CDCl_3$): δ 7.26 (m, 3H), 7.13 (m, 4H), 7.07 (d, 2H, J=8.4 Hz), 6.91 (m, 4H), 4.98 (m, 1H), 4.56 (m, 1H), 3.92 (s, 2H), 3.72 (s, 3H), 3.05 (br dq, 2H, J=13.6 Hz, J=5.2 Hz), 1.42 (s, 9H).

Step 3:

(S)-2-tert-Butoxycarbonylamino-3-{4-[4-(4-chloro-benzyl)-phenoxy]-phenyl}-propionic acid A mixture of the product (0.106 g, 0.214 mmol) in step 2 and NaOH (0.0427 g, 1.07 mmol) in THF (1.5 mL) and $H_2O$ (0.5 mL) was stirred at ambient temperature for 20 h. After removing the THF in vacuo and adding $H_2O$ (1.5 mL), the pH was adjusted to around 4 with 5N HCl to give a white gum. The aqueous layer was decanted off, diethyl ether was added, and then the ether was removed in vacuo to afford the crude acid as a white solid (0.111 g, 108%).

Step 4:

S)-2-Amino-3-{4-[4-(4-chloro-benzyl)-phenoxy]-phenyl}-propionic acid hydrochloride A solution of the product (0.109 g, 0.226 mmol) in step 3 in 4N hydrogen chloride in 1,4-dioxane (3.0 mL, 12.0 mmol) was stirred for 2 h at ambient temperature. The solution was diluted with diethyl ether (3 mL) and a white solid precipitated. The liquid was decanted off and the ether step was repeated two more times. The solid was dried in a 50° C. vacuum oven for 18 h to give the desired product as an white solid (0.056 g, 59%):

$^1$H NMR ($CD_3OD$): δ 7.27 (d, 4H, J=8.4 Hz), 7.18 (d, 4H, J=8.4 Hz), 6.94 (m, 4H), 4.22 (m, 1H), 3.94 (s, 2H), 3.28 (m, 1H), 3.14 (m, 1H). MS; m/z 380 $(M–H)^+$.

Example 6

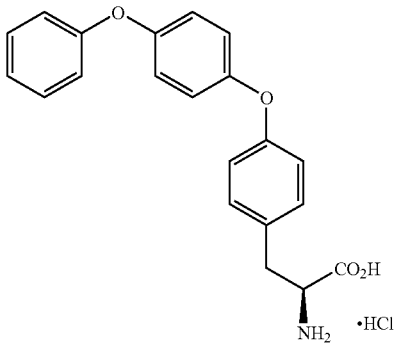

Step 1:

Methyl (2S)-2-[(tert-Butoxycarbonyl)amino]-3-[4-(4-phenoxyphenoxy)phenyl]Propanoate To a solution of Boc-L-Tyrosine methyl ester (2.37 g, 8.0 mmol), 4-phenyoxyphenylboronic acid (2.57 g, 12.0 mmol) and pyridine (3.16 g) in $CH_2Cl_2$ (200 mL) was added copper (II) acetate (1.46 g, 8.0 mmol). After stirring at rt for 24 h, the reaction mixture was concentrated in vacuo. The remaining material was dissolved in EtOAc (200 mL) and this solution was washed with water (2×100 mL). The organic layer was concentrated in vacuo and the crude product was purified by chromatography (7:3 hexane/ethyl acetate) to give 2.39 g of product (64%). $^1$H NMR (400 MHz, $CDCl_3$) δ 1.42 (s, 9H), 2.95-3.14 (m, 2H), 3.72 (s, 3H), 4.57 (q, J=7.2 Hz, 1H), 5.00 (br d, J=8.0 Hz, 1H), 6.90-7.11 (m, 11H), 7.30-7.36 (m, 2H).

Step 2:

(2S)-2-[(tert-Butoxycarbonyl)amino]-3-[4-(4-phenoxyphenoxy)phenyl]propanoic Acid To a solution of the methyl ester from step 1 (0.45 g, 0.97 mmol) in MeOH (10 mL) was added a solution of NaOH (0.06 g) in water (10 mL). After stirring at rt overnight the reaction mixture was concentrated in vacuo then the remaining material was dissolved in water (20 mL). Conc. HCl was added until the aqueous solution was acidic which caused material to precipitate out of solution. The mixture was extracted with EtOAc (50 mL). The EtOAc solution was washed once with water (50 mL) then was concentrated in vacuo to give 0.38 g of product (87%). $^1$H NMR (400 MHz, $CDCl_3$) δ 1.42 (s, 9H), 2.96-3.22 (m, 2H), 4.59 (br q, J=6.0 Hz, 1H), 4.97 (br d, J=8.0 Hz, 1H), 6.89-7.17 (m, 11H), 7.28-7.35 (m, 2H); LCMS; 99%, ESI$^+$, Calcd: 449.51 m/z. Found 350.6 (M+H−Boc) m/z.

Step 3:

(2S)-2-Amino-3-[4-(4-phenoxyphenoxy)phenyl]propanoic acid hydrochloride

To the carboxylic acid from step 2 (65 mg) was added 4.0 M HCl in dioxane (1.0 mL). After 3 h, the dioxane was removed to give 58 mg of product. $^1$H NMR (400 MHz, DMSO-$d_6$) δ 3.11-3.28 (m, 2H), 4.20 (t, J=6.0 Hz, 1H), 6.94-7.15 (m, 9H), 7.27-7.32 (m, 2H), 7.36-7.42 (m, 2H); LCMS; 99%, ESI$^-$, Calcd: 349.39 m/z. Found 348.5 (M−1) m/z.

Example 7

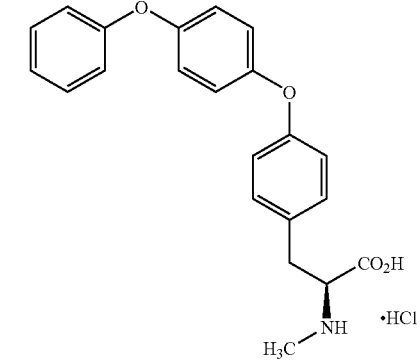

Step 1:

(2S)-2-[(tert-Butoxycarbonyl)(methyl)amino]-3-[4-(4-phenoxyphenoxy)phenyl]propanoic Acid NaH (60% dispersion in mineral oil, 0.10 g, 2.5 mmol) was washed twice with hexane then to this material was added THF (15 mL). This mixture was cooled in an ice water bath and a solution of the acid (0.28 g, 0.6 mmol) in THF (15 mL) and added. After stirring for 15 minutes, to this mixture was added iodomethane (0.70 g, 5.0 mmol) and the reaction mixture was allowed to warm to rt. After stirring overnight at rt the mixture was concentrated in vacuo. The remaining material was partitioned between water (25 mL) and EtOAc (25 mL). The aqueous solution was neutralized with conc. HCl, sodium thiosulfate (2.0 g) was added and this solution was extracted with EtOAc (50 mL). The EtOAc solution was washed with water (50 mL) then was concentrated in vacuo to give 0.23 g of product.

Analysis indicated the reaction was incomplete so the reaction was repeated on 0.15 g of product using 6.0 eq. of NaH and 12.0 eq. of iodomethane to give 0.11 g of material that was purified by chromatography (99.4:0.5:0.1 EtOAc/2-propanol/AcOH) to give 0.09 g of product. $^1$H NMR (400 MHz, $CDCl_3$) δ 2.68-2.81 (m, 3H), 2.96-3.15 (m, 1H), 3.23-3.33 (m, 1H), 4.55-4.82 (m, 1H), 6.91-7.20 (m, 11H), 7.30-7.36 (m, 2H); LCMS; 99%, ESI$^-$, Calcd: 463.54 m/z. Found 462.8 (M−1) m/z.

Step 2:

(2S)-2-(Methylamino)-3-[4-(4-phenoxyphenoxy)phenyl]propanoic Acid hydrochloride

To the acid from step 1 (84 mg) was added 4.0 M HCl in dioxane (1.0 mL). After 3 h, the dioxane was removed to give 74 mg of product. $^1$H NMR (400 MHz, DMSO-$d_6$) δ 2.57 (s, 3H), 3.15 (dd, J=14.2, 6.8 Hz, 1H), 3.25 (dd, J=14.2, 4.8 Hz, 1H), 4.20 (t, J=6.0 Hz, 1H), 6.96-7.15 (m, 9H), 7.27-7.42 (m, 4H); LCMS; 100%, ESI$^-$, Calcd: 363.42 m/z. Found 362.5 (M−1) m/z.

Example 8

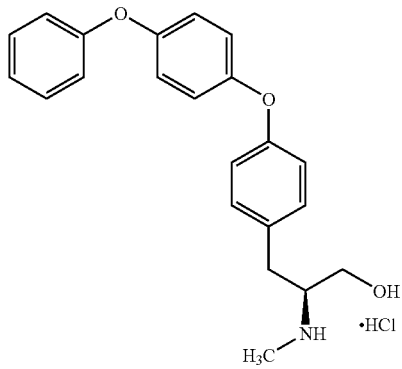

Step 1:

tert-Butyl{(1S)-1-[4-(4-phenoxyphenoxy)benzyl]-2-hydroxyethyl}methylcarbamate

To a solution of the acid from step 1, Example X (50 mg) in THF (2 mL) was added a solution of 1.0 M BH$_3$ in THF (0.2 mL). After 1 h, TLC analysis indicated some starting material remained so more 1.0 M BH$_3$ in THF (0.2 mL) was added. After another hour TLC analysis indicated all starting material had been consumed. MeOH (5 mL) was added and the reaction mixture was concentrated in vacuo. MeOH (5 mL) was added to the remaining material and then again removed in vacuo to give 53 mg of material. This material was purified by chromatography (1:1 hexane/ethyl acetate) to give 26 mg of product. $^1$H NMR (400 MHz, CDCl$_3$) δ 1.25-1.48 (m, 9H), 1.64 (br s, 1H), 2.58-2.93 (m, 5H), 3.60-3.78 (m, 2H), 4.08-4.36 (m, 1H), 6.90-7.36 (m, 13H); LCMS; 100%, ESI$^+$, Calcd: 449.55 m/z. Found 350.7 (M+H−Boc) m/z.

Step 2:

(2S)-2-(Methylamino)-3-[4-(4-phenoxyphenoxy)phenyl]propan-1-ol hydrochloride

To the alcohol from step 1 (26 mg) was added 4.0 M HCl in dioxane (0.5 mL). After 3 h, the dioxane was removed to give 22 mg of product. $^1$H NMR (400 MHz, DMSO-d$_6$) δ 2.57-2.63 (m, 3H), 2.80 (dd, J=13.6, 10.4 Hz, 1H), 3.02 (dd, J=13.6, 4.8 Hz, 1H), 3.23-3.43 (m, 2H), 3.55-3.62 (m, 1H), 5.43 (br s, 1H), 6.96-7.16 (m, 9H), 7.28-7.43 (m, 4H), 8.70 (br s, 1H), 8.91 (br s, 1H); LCMS; 100%, ESI$^+$, Calcd: 349.43 m/z. Found 350.9 (M+1) m/z.

Example 9

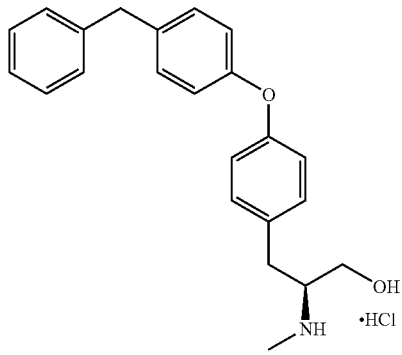

Step 1:

Methyl (2S)-2-[(tert-Butoxycarbonyl)amino]-3-[4-(4-benzoylphenoxy)phenyl]Propanoate A mixture of Boc-Tyr-OMe (0.80 g, 2.7 mmol), 4-fluorobenzophenone (0.80 g, 4.0 mmol) and potassium carbonate (1.11 g, 8.0 mmol) in DMF (30 mL) was heated to 100° C. After 42 h, the reaction mixture was allowed to cool to rt. DMF was removed in vacuo and the remaining material was partitioned between EtOAc (50 mL) and water (50 mL). This gave an emulsion that was allowed to sit overnight. The following day the layers had mostly separated and so the organic layer was concentrated in vacuo to give 1.32 g of material. This material was purified by chromatography (4:1 hexane/ethyl acetate) to give 0.69 g of product. $^1$H NMR (400 MHz, CDCl$_3$) δ 1.43 (s, 9H), 2.98-3.19 (m, 2H), 3.74 (s, 3H), 4.60 (q, J=6.8 Hz, 1H), 5.03 (br d, J=7.6 Hz, 1H), 6.98-7.05 (m, 4H), 7.14-7.19 (m, 2H), 7.45-7.51 (m, 2H), 7.55-7.61 (m, 1H), 7.75-7.84 (m, 4H).

Step 2:

Methyl (2S)-2-[(tert-Butoxycarbonyl)amino]-3-[4-(4-benzylphenoxy)phenyl]Propanoate To a solution of the benzoyl derivative from step 1 (0.20 g, 0.4 mmol) in AcOH (5.0 mL) was added 10% Pd/C (20 mg) and the mixture was hydrogenated at 40 psi. After 2 h, TLC analysis (7:3 hexane/EtOAc) indicated the reaction was incomplete so more 10% Pd/C (20 mg) was added and the hydrogenation of the reaction mixture at 40 psi was continued overnight. After hydrogenation for a total of 22 h, the reaction mixture was filtered through Celite 521 (2.0 g) and the filtrate was concentrated in vacuo to give 0.19 g of material. $^1$H NMR (400 MHz, CDCl$_3$) δ 1.42 (s, 9H), 2.95-3.12 (m, 2H), 3.71 (s, 3H), 3.96 (m, 2H), 4.56 (q, J=6.8 Hz, 1H), 4.99 (br d, J=7.6 Hz, 1H), 6.88-6.94 (m, 4H), 7.04-7.32 (m, 9H).

Step 3:

(2S)-3-[4-(4-Benzylphenoxy)phenyl]-2-(methylamino)propan-1-ol

To a solution of the benzyl derivative from step 2 (0.19 g, 0.4 mmol) in 1,2-dimethoxyethane (15 mL) was added NaBH$_4$ (0.15 g, 4.0 mmol) and BF$_3$.OEt$_2$ (0.28 g, 2.0 mmol). After stirring at rt for 96 h, to the solution was slowly added MeOH (10 mL) and the reaction mixture was concentrated in vacuo. Twice MeOH (25 mL each time) was added and removed in vacuo. The remaining material was dissolved in EtOAc and washed with water. The EtOAc solution was concentrated in vacuo to give 0.15 g of material.

Chromatographic purification of this material was carried out using 1:1 hexane/EtOAc to give what is apparently a mixture of diastereomers of the borane-amine adduct of the N-methylamino alcohol (0.11 g). A mixture of this material and 10 wt. % Pd/C (40 mg) in AcOH (5 mL) was hydrogenated at rt for 24 h. The reaction mixture was filtered through Celite 521 and the filtrate was concentrated in vacuo to give 0.11 g of material.

To this material was added ether (50 mL), water (25 mL) and NaOH (0.20 g). The ether layer was washed with water (25 mL) then was concentrated in vacuo to give 0.08 g of crystalline material. This material was dissolved in ether then hexane was added. This solution was concentrated in vacuo and once most of the ether had been removed in vacuo the product appeared to crystallize out of solution. Before all hexane had been removed the concentration in vacuo was stopped and the remaining hexane solution was removed by pipet. The remaining material was dissolved again in ether, hexane was added, and the solution was concentration in vacuo. Again the product appeared to crystallize from solution and before all hexane had been removed the concentration was stopped and the remaining hexane solution was removed by pipet. The remaining material was placed under high vacuum to give 0.06 g of the N-methylamino alcohol. $^1$H NMR (400 MHz, CDCl$_3$) δ 2.02 (br s, 2H), 2.41 (s, 3H), 2.65-2.81 (m, 3H), 3.35 (dd, J=10.6, 4.8 Hz, 1H), 3.64 (dd, J=10.6, 3.2 Hz, 1H), 3.96 (s, 3H), 6.89-6.95 (m, 4H), 7.09-7.32 (m, 9H).

Step 4:

(2S)-3-[4-(4-Benzylphenoxy)phenyl]-2-(methylamino)propan-1-ol hydrochloride

To a solution of the N-methylamino alcohol from step 3 (0.06 g, 0.2 mmol) in ether (50 mL) was added 2.0 M HCl in ether (5.0 mL). Immediately material precipitated out of solution. After 1 h, the precipitate was isolated by filtration and the collected solid was washed with ether to give 55 mg of product. $^1$H NMR (400 MHz, DMSO-d$_6$) δ 2.59 (s, 3H), 2.80 (dd, J=13.4, 10.4 Hz, 1H), 3.03 (dd, J=13.4, 4.4 Hz, 1H), 3.25 (br s, 1H), 3.30-3.43 (m, 2H), 3.59 (d, J=12.0 Hz, 1H), 3.92 (s, 2H), 5.43 (s, 1H), 6.90-6.97 (m, 4H), 7.16-7.32 (m, 9H), 8.78 (br s, 1H), 9.04 (br s, 1H); LCMS; 100%, APCI$^+$, Calcd: 347.46 m/z. Found 348.2 (M+H) m/z.

Example 10

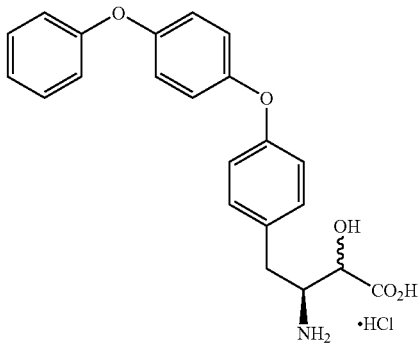

Step 1:

tert-Butyl {(1S)-1-formyl-2-[4-(4-phenoxyphenoxy)phenyl]ethyl}carbamate

To a solution of the methyl ester from step 1, Example X (0.46 g) in toluene (5.0 mL) cooled in a dry ice/acetone bath was added a solution of 1.0 M DIBAL-H in hexanes (2.5 mL) over three minutes. Two minutes after completion of the addition of the DIBAL-H solution, MeOH (0.2 mL) was added. The reaction mixture was poured into a solution of 5 mL of 20% sodium potassium tartrate. After a few minutes the organic layer became a gel so sufficient EtOAc and 20% sodium potassium tartrate were added until the gel dissolved. The organic layer was concentrated in vacuo to give 0.37 g of material. $^1$H NMR (400 MHz, CDCl$_3$) δ 1.44 (s, 9H), 3.09 (t, J=5.8 Hz, 2H), 4.43 (q, J=5.8 Hz, 1H), 5.06 (br d, J=5.2 Hz, 1H), 6.91-7.36 (m, 13H), 9.63 (s, 1H).

Step 2:

tert-Butyl {(1S)-2-cyano-1-[4-(4-phenoxyphenoxy)benzyl]2-hydroxyethyl}carbamate

To the product from step 1 (0.35 g) was added a solution of sodium metabisulfite (0.29 g) in water (1.0 mL). It appeared that little if any of the starting material went into solution. Nevertheless, to this solution was added a solution of NaCN (0.08 g) in water (1.0 mL). After stirring for an hour it still appeared that little if any of the starting material had gone into solution. Therefore to this solution was added sufficient MeOH to dissolve the starting material. However this caused some solid material to come out of solution. Some water was added to try to dissolve this solid but then it appeared the starting material started to oil out of solution. This nonhomogeneous reaction mixture was stirred at rt for another 4 h, then was partially concentrated in vacuo. The remaining material was partitioned between EtOAc (50 mL) and water (25 mL). The organic layer was concentrated in vacuo to give 0.27 g of material. $^1$H NMR analysis of this material indicated that it contained a mixture of starting aldehyde and desired cyanohydrin.

To a solution of this material (0.27 g) in CH$_2$Cl$_2$ (5.0 mL) was added trimethylsilyl cyanide (0.15 g). After 2 h, TLC analysis (7:3 hexane/EtOAc) indicated little reaction was taking place so some TEA (0.15 g) was added. TLC analysis 15 minutes later showed all starting material had been consumed. The reaction mixture was concentrated in vacuo and to the remaining material was added 1 M HCl (10 mL) and THF (10 mL). Since the solution was cloudy more THF was added to give a homogeneous solution. After 2 h at rt, the reaction mixture was partially concentrated in vacuo and the remaining material was extracted with EtOAc (50 mL). The EtOAc solution was concentrated in vacuo to give 0.23 g of material. This material was purified by chromatography (2:1 hexane/EtOAc) to give 0.11 g of the cyanohydrin as a mixture of diastereomers. $^1$H NMR (400 MHz, CDCl$_3$) δ 1.44 (s, 9H), 2.80-2.99 (m, 1.5H), 3.04-3.16 (m, 0.5 h), 3.84 (br s, 0.5H), 4.14 (q, J=8.4 Hz, 0.5H), 4.48 (dd, J=8.0, 2.8 Hz, 0.5H), 4.56 (br s, 0.5H), 4.75-4.90 (m, 0.5H), 4.88 (d, J=6.4 Hz, 0.5H), 5.00 (d, J=6.4 Hz, 0.5H), 5.33 (d, J=7.6 Hz, 0.5H), 6.93-7.03 (m, 8H), 7.06-7.12 (m, 1H), 7.17 (d, J=8.8 Hz, 2H), 7.30-7.37 (m, 2H); LCMS; 93%, ESI$^+$, Calcd: 460.53 m/z. Found 461.7 (M+H) m/z. Integration of the signals at 3.84 and 4.14 ppm as well as at 5.00 and 5.33 ppm indicated the ratio of the diastereomers was about 1.3 to 1.0. Later when the aldehyde was treated directly with trimethylsilyl cyanide, further workup gave material in which the ratio of diastereomers had increased to about 4.5 to 1.0. Signals due to the major diastereomer included those at 3.84, 4.56, 4.75-4.90 and 5.00 ppm while signals due to the minor diastereomer included those 4.14, 4.48, 4.88 and 5.33 ppm.

Step 3:

(3S)-3-Amino-2-hydroxy-4-[4-(4-phenoxyphenoxy)phenyl]butanoic acid hydrochloride To material from step 2 (54 mg) was added 25% HCl (25 mL) and the mixture was heated to 80° C. After heating at 80° C. for 16 h, the reaction mixture was allowed to cool to rt and the insoluble material was collected by filtration to give 34 mg of product. $^1$H NMR (400 MHz, DMSO-d$_6$) δ 2.76-2.94 (m, 2H), 3.42-3.47 (m, 0.5 h), 3.52-3.57 (m. 0.5H), 3.80 (d, J=8.0, 2.8 Hz, 0.5H), 4.56 (br s, 0.5H), 4.75-4.90 (m, 0.5H), 4.88 (d, J=6.4 Hz, 0.5H), 4.02 (d, J=3.6 Hz, 0.5H), 6.92-7.08 (m, 8H), 7.17 (t, J=5.8 Hz, 1H), 7.24-7.30 (m, 2H), 7.36-7.41 (m, 2H); LCMS; 92%, ESI⁻, Calcd: 379.42 m/z. Found 378.7 (M−1) m/z.

Example 11

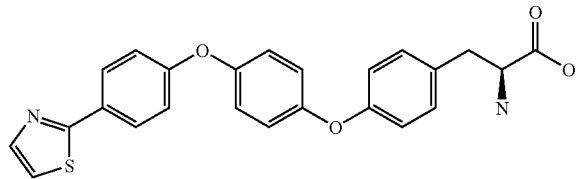

Step 1:

(S)-2-tert-Butoxycarbonylamino-3-(4-iodo-phenyl)-propionic acid methyl ester

To a solution of 4-iodo-L-phenalanine (2 g, 5.1 mmol) in benzene-methanol (6:5, 20 mL) was added (trimethylsilyl)diazomethane (2M in ether, 3 mL, 6 mmol), and then stirred for 1 h. The solvents were removed to yield the title compound (1) (2.0 g, 99%). ¹HNMR (400 MHz, CDCl₃) δ 3.00 (m, 2H), 3.72 (s, 3H), 4.56 (m, 1H), 4.96 (m, 1H), 6.86 (d, J=8 Hz, 2H), 7.61 (d, J=8 Hz, 2H).

Step 2:

2-(4-Methoxy-phenyl)-thiazole

A mixture of 2-bromothiazole (2.0 g, 12.2 mmol), (4-methoxyphenyl)boronic acid (1.9 g, 12.8 mmol), K₂CO₃ (5.0 g, 36.5 mmol) and (Ph₃P)₄Pd (0.7 g, 0.61 mmol) in dioxane (40 mL) was refluxed for 16 h. After the solids were filtered off, the filtrate was concentrated in vacuo. The residue was purified by a column chromatography on silica gel to yield the title compound (1.1 g, 50%). ¹HNMR (400 MHz, CDCl₃) δ 3.86 (s, 3H), 6.96 (d, J=8.8 Hz, 2H), 7.25 (d, J=3.2 Hz, 1H), 7.81 (d, J=3.2 Hz, 1H), 7.90 (d, J=8.8 Hz, 2H), MS m/z 192 (M+1).

Step 3:

4-Thiazol-2-yl-phenol

To a solution of the product from step 2 (1.0 g, 5.23 mmol) in methylene chloride (25 ml) was slowly added boron tribromide (2.00 ml, 15.7 mmol) at −78° C., and stirred at −78° C. for 1 h. After it was stirred at room temperature for 16 h, the reaction mixture was poured into ice-water. The product was collected on a filter, washed with ether to yield the product from step two (0.84 g, 84%). ¹HNMR (400 MHz, CDCl₃) δ 6.88 (d, J=8.8 Hz, 2H), 7.67 (d, J=3.2 Hz, 1H), 7.79 (d, J=8.8 Hz, 2H), 7.85 (d, J=3.2 Hz, 1H), MS (ESI−) m/z 176 (M−1).

Step 4:

2-[4-(4-Methoxy-phenoxy)-phenyl]-thiazole

A mixture of product from step 3 (0.55 g, 3.1 mmol), iodoanisole (1.1 g, 4.6 mmol), CsCO₃ (3.0 g, 9.2 mmol), N,N-dimethylglycine HCl (0.43 g, 3.1 mmol) and CuI (0.3 g, 1.5 mmol) in dioxane (40 mL) was heated to 100° C. for 3 days. After the solids were filtered off, the filtrate was partitioned with EtOAc/H₂O, washed with brine, dried over Na₂SO₄ and concentrated in vacuo. The residue was purified by a column chromatography on silica gel to yield the title compound (0.75 g, 90%). ¹HNMR (400 MHz, CDCl₃) δ 3.82 (s, 3H), 6.90 (d, J=8 Hz, 2H), 6.97 (d, J=8.8 Hz, 2H), 7.03 (d, J=8.8 Hz, 2H), 7.28 (d, J=3.6 Hz, 1H), 7.81 (d, J=3.6 Hz, 1H), 7.90 (d, J=8.8 Hz, 2H), MS m/z 284 (M+1).

Step 5:

4-(4-Thiazol-2-yl-phenoxy)-phenol

The title compound was prepared from the product from step 4 (0.74 g, 2.5 mmol) and BBr₃ (1M in CH₂Cl₂, 7.5 mL, 7.5 mmol) using the Step 2 procedure with 75% yield (0.5 g). ¹HNMR (400 MHz, CDCl₃) δ 6.78 (d, J=8 Hz, 1H), 6.84 (m, 3H), 6.95 (m, 4H), 7.29 (d, J=3.6 Hz, 1H), 7.83 (d, J=3.6 Hz, 1H), 7.88 (d, J=8.8 Hz, 2H).

Step 6:

(S)-2-tert-Butoxycarbonylamino-3-{4-[4-(4-thiazol-2-yl-phenoxy)-phenoxy]-phenyl}-propionic acid methyl ester The title compound was prepared from the product from step 5 (0.3 g, 1.1 mmol) and compound (1) (0.45 g, 1.1 mmol) using the Step 4 procedure with 62% yield (0.38 g). ¹HNMR (CDCl₃, 400 MHz) δ 3.04 (m, 2H), 3.72 (s, 3H), 4.56 (m, 1H), 4.98 (m, 1H), 6.94 (d, J=8 Hz, 2H), 7.00-7.10 (m, 8H), 7.30 (d, J=3.2 Hz, 1H), 7.83 (d, J=3.6 Hz, 1H), 7.92 (d, J=8.8 Hz, 2H).

Step 7:

(S)-2-tert-Butoxycarbonylamino-3-{4-[4-(4-thiazol-2-yl-phenoxy)-phenoxy]-phenyl}-propionic acid A solution of the product from step 6 (0.4 g, 0.72 mmol) and NaOH (62 mg, 1.54 mmol) in THF/water (1:1, 10 mL) was stirred at room temperature for 16 h. After the THF was removed, the aqueous solution was acidified with 10% HCl to pH=2, the solid was collected on a filter to yield the title compound (340 mg, 82%). ¹HNMR (CDCl₃) δ 1.42 (s, 9H), 3.15 (m, 2H), 4.57 (m, 1H), 5.00 (m, 1H), 6.95 (d, J=8.8 Hz, 2H), 7.02-7.15 (m, 6H), 7.17 (d, J=8.8 Hz, 2H), 7.30 (d, J=3.2 Hz, 1H), 7.85 (d, J=3.2 Hz, 1H), 7.91 (d, J=8.8 Hz, 2H).

Step 8:

(S)-2-Amino-3-{4-[4-(4-thiazol-2-yl-phenoxy)-phenoxy]-phenyl}-propionic acid

A solution of the product from step four (340 mg, 0.67 mmol) in dioxane (2 ml) was added 4M HCl in dioxane (0.5 ml, 2.1 mmol), and stirred at room temperature for 4 h. After the solvent was removed, the crude material was triturated with ether to afford the title compound (230 mg, 73%). ¹HNMR (DMSO-d₆) δ 3.12 (m, 2H), 4.15 (m, 1H), 7.00 (d, J=8 Hz, 2H), 7.02-7.15 (m, 4H), 7.17 (d, J=8 Hz, 2H), 7.13 (d, J=8 Hz, 2H), 7.75 (d, J=3.2 Hz, 1H), 7.89 (d, J=3.2 Hz, 1H), 7.97 (d, J=8.8 Hz, 2H). LC/MS 91%, MS m/z 433 (M+1).

Example 12

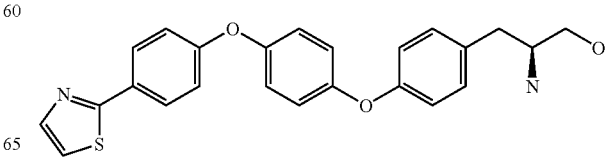

Step 9:

(S)-2-Amino-3-{4-[4-(4-thiazol-2-yl-phenoxy)-phenoxy]-phenyl}-propan-1-ol

To a solution of the product from step 8 (40 mg, 0.09 mmol) in THF (2 mL) was added borane THF (1M in THF, 0.2 mL, 0.17 mmol), and stirred at room temperature for 18 h. The reaction was quenched with 10% HCl, and stirred for 30 min. The aqueous solution was basified with 1N NaOH to pH to ~12. The solid was collected on a filter, triturated with ether to yield the title compound (18 mg, 50%). $^1$HNMR (CD$_3$OD) δ 2.62 (m, 1H), 2.81 (m, 1H), 3.11 (m, 1H), 3.35 (m, 1H), 3.57 (m, 1H), 6.96 (d, J=8 Hz, 2H), 7.02-7.09 (m, 6H), 7.23 (d, J=8 Hz, 2H), 7.57 (d, J=3.2 Hz, 1H), 7.81 (d, J=3.2 Hz, 1H), 7.93 (d, J=8.8 Hz, 2H). LC/MS 85%, MS m/z 419 (M+1).

Example 13

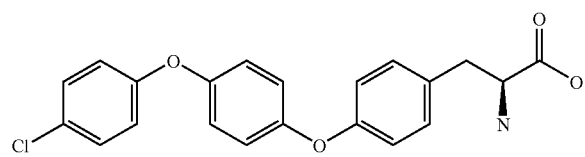

Step 1:

(S)-2-tert-Butoxycarbonylamino-3-{4-[4-(4-chloro-phenoxy)-phenoxy]-phenyl}-propionic acid methyl ester The title compound was prepared from 4-(4-chloro-phenoxy)-phenol (0.4 g, 1.8 mmol) and compound (1) (1.1 g, 2.7 mmol) using the Step 6 procedure of example 1 with 67% yield (0.6 g). $^1$HNMR (CDCl$_3$) δ 1.42 (s, 9H), 3.04 (m, 2H), 3.72 (s, 3H), 4.57 (m, 1H), 4.98 (m, 1H), 6.91 (d, J=2 Hz, 2H), 6.93 (d, J=2.8 Hz, 2H), 6.98 (s, 4H), 7.07 (d, J=8 Hz, 2H), 7.27 (d, J=8 Hz, 2H), MS m/z 398 (M−100).

Step 2:

(S)-2-tert-Butoxycarbonylamino-3-{4-[4-(4-chloro-phenoxy)-phenoxy]-phenyl}-propionic acid The title compound was prepared from step 1 product (0.1 g, 0.2 mmol) using the Step 7 procedure of example 1 with 93% yield (90 mg). $^1$HNMR (CDCl$_3$) δ 1.42 (s, 9H), 3.04 (m, 2H), 3.72 (s, 3H), 4.57 (m, 1H), 4.98 (m, 1H), 6.91 (d, J=2 Hz, 2H), 6.93 (d, J=2.8 Hz, 2H), 6.98 (s, 4H), 7.07 (d, J=8 Hz, 2H), 7.27 (d, J=8 Hz, 2H), MS m/z 398 (M−100).

Step 3:

(S)-2-Amino-3-{4-[4-(4-chloro-phenoxy)-phenoxy]-phenyl}-propionic acid

The title compound was prepared from step 2 product (0.1 g, 0.2 mmol) using the Step 8 procedure of example 1 with 99% yield (86 mg). $^1$HNMR (CD$_3$OD) δ 3.14 (m, 2H), 3.30 (s, 1H), 4.22 (m, 1H), 6.94 (d, J=8 Hz, 2H), 7.00 (d, J=8.8 Hz, 2H), 7.02 (s, 4H), 7.27 (d, J=8 Hz, 2H), 7.32 (d, J=8 Hz, 2H), LC/MS 99%, MS m/z 398 (M−100).

Step 4:

(S)-2-Amino-3-{4-[4-(4-chloro-phenoxy)-phenoxy]-phenyl}-propan-1-ol

The title compound was prepared from step 3 product (40 mg, 0.1 mmol) using the Step 8 procedure of example 1 with 88% yield (30 mg). $^1$HNMR (CD$_3$OD) δ 2.15 (dd, J=13.2, 8 Hz, 1H), 2.76 (dd, J=13.6, 5.2 Hz, 1H), 3.15 (m, 1H), 3.37 (dd, J=10.4, 6.8 Hz, 1H), 3.64 (dd, J=10.4, 4 Hz, 1H), 6.94 (m, 4H), 6.99 (s, 4H), 7.17 (d, J=8.8 Hz, 2H), 7.28 (d, J=8 Hz, 2H), LC/MS 90%, MS m/z 370 (M+1).

Example 14

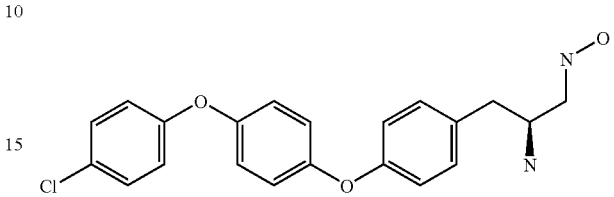

Step 1:

((S)-2-{4-[4-(4-Chloro-phenoxy)-phenoxy]-phenyl}-1-hydroxyaminomethyl-ethyl)-carbamic acid tert-butyl ester To a solution of (S)-2-tert-Butoxycarbonylamino-3-{4-[4-(4-chloro-phenoxy)-phenoxy]-phenyl}-propionic acid methyl ester (0.4 g, 0.8 mmol) in toluene (8 mL) was added DIBAL-H (1M in hexane, 1.8 mL, 1.8 mmol) at −78° C., and stirred at this temperature for 3 h. The reaction was added, and the mixture was allowed to warm to room temperature. The mixture was partitioned with EtOAc/H$_2$O, dried over Na$_2$SO$_4$ and concentrated to yield the aldehyde, which was dissolved in THF/MeOH (3:1, 10 mL). To this solution was added a mixture of NH$_2$OH.HCl and TEA in MeOH and stirred at room temperature for 16 h. The mixture was partitioned with EtOAc/H$_2$O, dried over Na$_2$SO$_4$ and concentrated to yield the title compound (0.24 g, 62%). $^1$HNMR (CDCl$_3$) 1.42 (s, 9H), 2.81 (m, 1H), 3.04 (m, 2H), 4.57 (m, 1H), 4.98 (m, 1H), 6.91-7.00 (m, 8H), 7.13 (m, 2H), 7.27 (d, J=8 Hz, 2H).

Step 2:

((S)-1-[(Acetoxy-acetyl-amino)-methyl]-2-{4-[4-(4-chloro-phenoxy)-phenoxy]-phenyl}-ethyl)-carbamic acid tert-butyl ester To a solution of the product from step 1 (0.2 g, 0.41 mmol) in pyridine (4 mL) was added acetic anhydride (0.13 g, 1.24 mmol) and stirred for 18 h. The reaction mixture was diluted with water, extracted with EtOAc, washed with 1 N HCl and water. After dried over Na$_2$SO$_4$, the title compound (0.2 g) was obtained with 75% yield. $^1$HNMR (CDCl$_3$) δ 1.40 (s, 9H), 2.01 (s, 3H), 2.20 (s, 3H), 2.83 (m, 2H), 3.65 (m, 1H), 3.88 (m, 1H), 4.01 (br, 1H), 4.68 (m, 1H), 6.91 (m, 4H), 6.98 (s, 4H), 7.14 (d, J=8 Hz, 2H), 7.27 (d, J=8 Hz, 2H), MS m/z 469 (M−100).

Step 3:

((S)-1-[(Acetyl-hydroxy-amino)-methyl]-2-{4-[4-(4-chloro-phenoxy)-phenoxy]phenyl}-ethyl)-carbamic acid tert-butyl ester To a solution of the product from step 2 (0.12 g, 0.21 mmol) in methanol (5 mL) was added NaOMe (25% in MeOH, 0.23 g, 1.1 mmol) at 0° C. and stirred at room temperature for 4 h. After the methanol was removed, the residue was partitioned in EtOAc/H$_2$O, dried over Na$_2$SO$_4$ and concentrated to yield the title compound (0.1 g, 90%). $^1$HNMR (CDCl$_3$) δ 1.40 (s, 9H), 2.10 (s, 3H), 2.81 (m, 2H), 3.05 (m, 1H), 4.11 (m, 1H), 4.01 (br, 1H), 4.66 (m, 1H), 6.91 (m, 4H), 6.98 (s, 4H), 7.14 (d, J=8 Hz, 2H), 7.27 (d, J=8 Hz, 2H), MS m/z 427 (M–100).

Step 4:

(S)-2-Amino-3-{4-[4-(4-chloro-phenoxy)-phenoxy]-phenyl}-propionic acid

The title compound was prepared from step 3 product (0.12 g, 0.2 mmol) using the Step 8 procedure of example 1 with 62% yield (60 mg). $^1$HNMR (DMSO-$d_6$) δ 2.97 (m, 1H), 3.06 (m, 1H), 3.20 (m, 1H), 3.47 (m, 1H), 3.83 (m, 1H), 7.05 (m, 8H), 7.34 (d, J=8 Hz, 2H), 7.43 (d, J=8 Hz, 2H), LC/MS 99%, MS m/z 385 (M+1).

Example 15

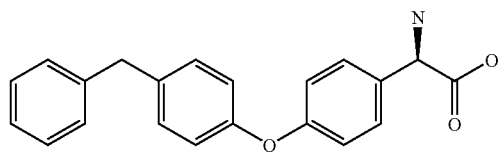

Step 1:

(R)-tert-Butoxycarbonylamino-(4-hydroxy-phenyl)-acetic acid methyl ester

To a solution of D-p-phenylglycine hydrochloride (3.0 g, 13.8 mmol) and NaHCO$_3$ (3.0 g, 27.6 mmol) in THF/H$_2$O (2:8, 30 mL) was added di-t-butyl carbonate (3.6 g, 16.5 mmol) and stirred at room temperature for 18 h. After the THF was removed, the residue was partitioned with EtOAc/H$_2$O, dried over Na$_2$SO$_4$ and concentrated to yield the title compound (3.1 g, 77%). $^1$HNMR (CDCl$_3$) δ 1.44 (s, 9H), 3.71 (s, 3H), 5.22 (d, J=6.8 Hz, 1H), 5.53 (br, 1H), 6.91 (m, 4H), 6.75 (d, J=8 Hz, 2H), 7.21 (br, 2H).

Step 2:

(R)-[4-(4-Benzyl-phenoxy)-phenyl]-tert-butoxycarbonylamino acetic acid methyl ester The title compound was prepared from the product from step 1 (1.3 g, 4.6 mmol) and 4-iododiphenylmethane (2.0 g, 6.9 mmol) using the Step 4 procedure of example 1 with 50% yield (1.1 g). $^1$HNMR (CDCl$_3$) 1.43 (s, 9H), 3.73 (s, 3H), 3.97 (s, 2H), 5.29 (m, 1H), 5.50 (m, 1H), 6.94 (m, 4H), 7.15 (d, J=6.8 Hz, 2H), 7.20 (m, 3H), 7.30 (m, 4H), MS m/z 448 (M+1).

Step 3:

(R)-[4-(4-Benzyl-phenoxy)-phenyl]-tert-butoxycarbonylamino acetic acid

The title compound was prepared from the product from step 2 (1.3 g, 2.2 mmol) and NaOH (0.2 g, 4.4 mmol) using the Step 7 procedure of example 1 with 99% yield (1.0 g). $^1$HNMR (CDCl$_3$) δ 1.43 (s, 9H), 3.86 (s, 2H), 4.71 (br, 1H), 4.93 (br, 1H), 5.76 (br, 1H), 6.75 (m, 4H), 7.02 (d, J=6.8 Hz, 2H), 7.13 (m, 3H), 7.23 (m, 4H), MS m/z 432 (M–1).

Step 4:

(R)-Amino-[4-(4-benzyl-phenoxy)-phenyl]-acetic acid hydrochloride

The title compound was prepared from the product from step 3 (1.0 g, 2.3 mmol) using the Step 8 procedure of example 1 with 50% yield (0.43 g). $^1$HNMR (DMSO-$d_6$) δ 3.92 (s, 2H), 5.02 (s, 1H), 6.96 (d, J=8 Hz, 2H), 7.01 (d, J=8.8 Hz, 2H), 7.19-7.31 (m, 7H), 7.52 (d, J=8.8 Hz, 2H), 8.90 (br, 2H), LC/MS 93%, MS m/z 332 (M–1).

Example 16

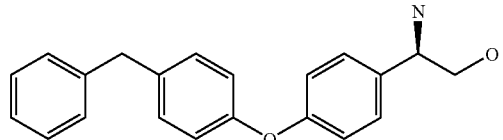

Step 5:

(R)-2-Amino-2-[4-(4-benzyl-phenoxy)-phenyl]-ethanol

The title compound was prepared from the product from step 4 (1.0 g, 2.3 mmol) using the Step 9 procedure of example 1 with 50% yield (0.43 g). $^1$HNMR (CDCl$_3$) δ 3.53 (m, 1H), 3.71 (br, 1H), 3.96 (s, 2H), 4.02 (br, 1H), 6.91 (d, J=8 Hz, 2H), 6.94 (d, J=8.8 Hz, 2H), 7.14 (d, J=8 Hz, 2H), 7.20 (m, 3H), 7.29 (m, 4H).

Example 17

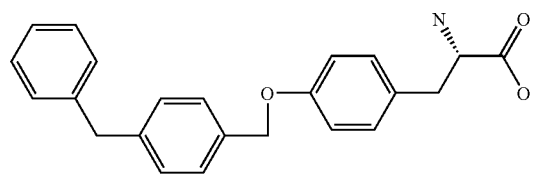

Step 1:

(4-benzyl-phenyl)-methanol

To a solution of diphenylmethyl-4-carboxylic acid (6 g, 37.7 mm) in THF (200 mL) was added LiAlH$_4$ (1.5 g, 59.5 mm) slowly over 5 minutes at room temperature. The reaction mixture was refluxed for 16 hours and then cooled down to room temperature. At 4° C., the reaction mixture was diluted with diethyl ether (50 mL), followed by a successive addition of 1.5 ml of water, 1.5 ml of 15% NaOH and 4.5 mL of water. After stirring at room temperature for 30 minutes, white precipitate formed was removed by filtration and the filtrate was concentrated under reduced pressure to give the title compound as a white solid (5.8 g, 99%); MS: m/z 199 (M+1);
$^1$H NMR (400 HMz, CDCl$_3$, ppm) δ 3.98 (s, 2H), 4.65 (d, J=5.2, 2H), 7.17-7.21 (m, 5H), 7.25-7.30 (m, 4H).

Step 2:

(S)-3-[4-Benzyl-phenyloxy)-phenyl]-2-tert-butoxycarbonylamino-propionic acid methyl ester To a mixture of Boc-L-Tyr-OMe 90.59 g, 2 mm), DIAD (0.4 g, 2 mm) and triphenyl-phosphine (0.51 g, 2 mm) in THF (5 mL) was added (4-benzyl-phenyl)-methanol dissolved in THF (2 mL) at room temperature. The reaction was stirred at room temperature for 16 hours followed by addition of water (20 mL). The mixture was extracted with ethyl acetate and the combined organic layers was washed with brined, dried over anhydrous Na2SO4 and evaporated in vacuo to furnish the title compound as a light yellow oil (0.68 g, yield 71.2%); MS: m/e 476 (M+1); $^1$H NMR (400 HMz, CDCl$_3$, ppm) δ 1.42 (s, 9H), 3.02-3.04 (b, 2H), 3.70 (s, 3H), 3.99 (s, 2H), 4.55 (b, 1H), 4.86 (m, 1H), 4.99 (s, 2H), 6.89 (dd, J=2, 7.8 Hz, 2H), 7.02 (d, J=8.8 Hz, 2H), 7.18-7.21 (m, 5H), 7.26-7.30 (m, 3H). 7.34 (d, 8 Hz, 2H).

Step 3:

(S)-2-Amino-3-[4-(4-benzyl-phenyloxy)-phenyl]-propionic acid

To a solution of (S)-3-[4-Benzyl-phenyloxy)-phenyl]-2-tert-butoxycarbonylamino-propionic acid methyl ester (0.125 g, 0.26 mm) in methanol (3 mL) was added 1 N NaOH (0.88 mL, 0.88 mm) and the reaction was heated at 65° C. for 4 hours, followed by evaporation of the solvent under reduced pressure. To the residue was added 4 N HCl in dioxin (3 mL) and the reaction as stirred at room temperature for 2 hours. The solvent was stripped off under reduced pressure and water was added to the residue, followed by adjusting the pH to 6-7 with 1 N NaOH. The desired compound was extracted with ethyl acetate and the combined organic payers was washed with brine, dried over anhy. Na2SO4, and evaporated under reduced pressure to yield the title compound as a white solid (35 mg, yield 37%); MS; m/e 362 (M+1)

$^1$H NMR (400 HMz, CD$_3$OD, ppm) δ 2.86 (dd, J=2.81-2.87 (m, 1H), 3.07 (dd, J=4.8, 12.8, 1H), 3.96 (s, 2H), 4.20 (b, 1H), 4.99 (s, 2H), 6.85 (d, J=8 Hz, 1H), 7.10-7.12 (m, 2H), 7.15-7.19 (m, 5H), 7.23-7.27 (m, 2H), 7.32 (d, J=8.4 Hz, 2H).

Example 18

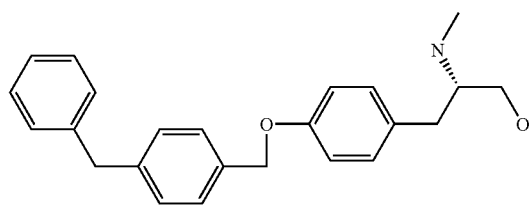

Step 1:

(S)-3-[4-(4-benzyl-phenyloxy)-phenyl]-2-methylamino-propan-1-ol

To a solution of (S)-3-[4-Benzyl-phenyloxy)-phenyl]-2-tert-butoxycarbonylamino-propionic acid methyl ester (0.13 g, 0.27 mm) in THF (10 mL) was added LiAlH$_4$ (0.3 g, 8.1 mm) slowly at room temperature. The reaction mixture was refluxed for 16 hours and then cooled down to room temperature. At 4° C., the reaction was diluted with diethyl ether (20 mL), followed by a successive addition of 0.3 ml of water, 0.3 ml of 15% NaOH and 0.9 mL of water. After stirring at room temperature for 30 minutes, white precipitate formed was removed by filtration and the filtrate was concentrated under reduced pressure to give the title compound as a white solid (0.095 g, 97%); MS; m/e 362 (M+1); $^1$H NMR (400 HMz, CDCl$_3$, ppm) δ 3.39 (s, 3H), 2.65-2.74 (m, 3H), 3.23 (dd, J=4.6, 10.4 Hz, 2H), 3.63 (dd, J=4, 11.6 Hz, 2H), 3.99 (s, 2H), 5.00 (s, 2H), 6.89-6.92 (m, 2H), 7.08-7.01 (m, 2H), 7.19 (t, J=7.6 Hz, 4H) 7.25-7.30 (m, 3H), 7.34 (d, J=8.4 Hz, 2H).

Example 19

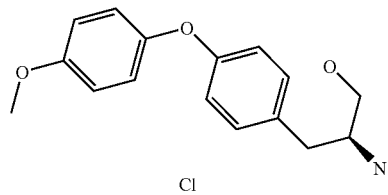

Step 1:

(S)-4-[4-(4-Methoxyphenoxy)-benzyl]-2,2-dimethyl-oxazolidine-3carboxylic acid tert-butyl ester To a solution of (S)-4-(4-Hydroxy-benzyl)-2,2-dimethyl-oxazolidine-3-carboxylic acid tert-butyl ester (150 mg, 0.5 mmol, 1 eq.)), 4-iodoanisole (180 mg, 0.75 mmol, 1.5 eq.) in dioxane (4 ml) was added CuI(I) (20 mg, 0.05 mmol, 0.1 eq.), N,N-dimethylglycine (30 mg, 0.15 mmol, 0.3 eq.) and cesium carbonate (500 mg, 1.5 mmol, 3 eq.). The resulting mixture was stirred under Ar at reflux overnight. After cooling to room temperature, the volatile material was removed under reduced pressure to give a residue, which was partitioned between water (10 ml) and ethyl acetate (10 ml). The ethyl acetate layer was separated and dried over anhydrous MgSO$_4$. Evaporation of solvent under reduced pressure gave a residue, which was passed through a plug of silica gel using dichloromethane (50 ml) as eluent to give 106 mg of desired product (51% yield).

Step 2:

(S)-2-Amino-3-[4-(4-methoxyphenoxy)-phenyl]-propan-1-ol hydrochloric acid salt

To a solution of crude product obtained from step 1 (100 mg, 0.25 mmol, 1 eq.) in methanol (2 ml) was added 4N HCl in dioxane (2 ml, 8 mmol, 32 eq.). The resulting mixture was stirred at room temperature for 2 hr. And then the volatile material was removed under reduced pressure. The residue thus obtained was washed with ether (3×15 ml) to remove non-acidic impurities. After dried, 75 mg of desired product (HCl salt) was obtained as white solid (99% isolated yield).

$^1$H NMR (400 MHz, DMSO-d$_6$) 62.87 (m, 2H), 3.27-3.30 (m, 1H), 3.36-3.41 (m, 1H), 3.50-3.55 (m, 1H), 3.93 (s, 2H), 6.91-6.95 (m, 4H), 7.19-7.30 (m, 9H), 7.93 (s, brs, 2H); LCMS (UV, ESI), 274 (M+1), 95% purity.

Example 20

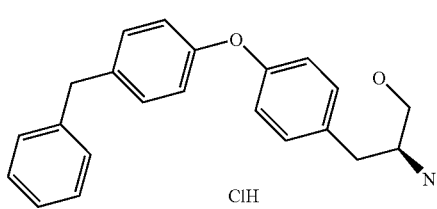

Step 1:

(S)-4-[4-(4-benzylphenoxy)-benzyl]-2,2-dimethyloxazolidine-3-carboxylic acid tert-butyl ester To a solution of (S)-4-(4-Hydroxy-benzyl)-2,2-dimethyl-oxazolidine-3-carboxylic acid tert-butyl ester (240 mg, 0.75 mmol, 1 eq. obtained from Brian Bock, Lot No: MCLS1172-077-1), 4-benzyliodobenzene (294 mg, 1 mmol, 1.3 eq.) in dioxane (4 ml) was added CuI(I) (30 mg, 0.75 mmol, 0.1 eq.), N,N-dimethylglycine (45 mg, 0.23 mmol, 0.3 eq.) and cesium carbonate (500 mg, 1.5 mmol, 3 eq.). The resulting mixture was stirred under Ar at reflux overnight. After cooling to room temperature, the volatile material was removed under reduced pressure to give a residue, which was partitioned between water (10 ml) and ethyl acetate (10 ml). The ethyl acetate layer was separated and dried over anhydrous MgSO$_4$. Evaporation of solvent under reduced pressure gave a residue, which was passed through a plug of silica gel using dichloromethane (50 ml) as eluent to give 350 mg of desired product containing the starting iodide, which was forwarded to the next step without further purification.

Step 2:

(S)-2-Amino-3-[4-(4-benzylphenoxy)-phenyl]-propan-1-ol hydrochloric acid salt To a solution of crude product obtained from step 1 (350 mg, 0.75 mmol, 1 eq.) in methanol (4 ml) was added 4N HCl in dioxane (2 ml, 8 mmol, 11 eq.). The resulting mixture was stirred at room temperature over night. And then the volatile material was removed under reduced pressure. The residue thus obtained was washed with ether (3×15 ml) to remove non-acidic impurities. After dried, 196 mg of desired product (HCl salt) was obtained as white solid (71% isolated yield over two steps). $^1$H NMR (400 MHz, DMSO-d$_6$) δ 2.87 (m, 2H), 3.27-3.30 (m, 1H), 3.36-3.41 (m, 1H), 3.50-3.55 (m, 1H), 3.93 (s, 2H), 6.91-6.95 (m, 4H), 7.19-7.30 (m, 9H), 7.93 (s, brs, 2H); LCMS (UV, ESI), 335 (M+1), 98% purity.

Example 21

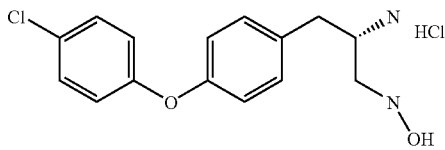

Step 1:

(S)-2-tert-Butoxycarbonylamino-3-[4-(4-chlorophenoxy)-phenyl]-propionic acid methyl ester To a solution of (S)-2-tert-Butoxycarbonylamino-3-[4-hydroxy-phenyl]-propionic acid methyl ester (2 g, 6.8 mmol, 1 eq.) in dioxane (20 ml) was added 4-bromochlorobenzene (1.95 g, 10 mmol, 1.5 eq.), CuI(I) (140 mg, 0.7 mmol, 0.1 eq.), N,N-dimethylglycine (220 mg, 2.1 mmol, 0.3 eq.) and cesium carbonate (4.6 g, 14 mmol, 3 eq.). The resulting mixture was stirred under Ar at reflux overnight. After cooling to room temperature, the volatile material was removed under reduced pressure to give a residue, which was partitioned between water and ethyl acetate. The ethyl acetate layer was separated and the aqueous layer was extracted with ethyl acetate (2×20 ml). The combined ethyl acetate layers were dried over anhydrous MgSO$_4$. Evaporation of solvent under reduced pressure gave a residue, which was purified by chromatography on silica gel using dichloromethane/MeOH (50:1) as eluent to give the desired product (587 mg, 21% yield).

Step 2:

{(S)-2-[4-(4-chloro-phenoxy)-phenyl]-1-formyl-ethyl}-carbamic acid tert-butyl ester To a solution of (S)-2-tert-Butoxycarbonylamino-3-[4-(4-chloro-phenoxy)-phenyl]-propionic acid methyl ester (107 mg, 0.26 mmol, 1 eq.) in toluene (5 ml) was added dropwise diisobutylaluminium hydride (1 M in hexane, 0.6 ml, 2.3 eq.) by a syringe with stirring under Ar at −78° C. After the addition was complete, the mixture was stirred at the same temperature for 2 hr and then AcOH (0.2 ml) was added. The mixture was allowed to warm to room temperature overnight. The mixture was partitioned between water and ethyl acetate. EA layer was separated and aqueous layer was extracted with EA. The combined EA layers were dried over anhydrous MgSO4. After the volatile material was removed, the desired product was obtained (68 mg, 70% yield). The product thus obtained was forward to the next step without any further purification.

Step 3:

{(S)-2-[4-(4-chloro-phenoxy)-phenyl]-1-hydroxyaminomethyl-ethyl}-carbamic acid tert-butyl ester To a solution of {(S)-2-[4-(4-chloro-phenoxy)-phenyl]-1-formyl-ethyl}-carbamic acid tert-butyl ester (68 mg, 0.18 mmol, 1 eq.) in THF (0.5 ml) and methanol (4 ml) was added hydroxylamine HCl salt (75 mg, 1 mmol, 5.6 eq.) followed by triethylamine (0.2 ml, 1.5 mmol, 8.3 eq.). The mixture was shaken in a shaker at room temperature overnight. Sodium cyanoborohydride (10 mg, 0.29 mmol, 1.6 eq.) was added in one portion. Then 4 N HCl in dioxane was added dropwise until the reaction mixture was acidic. The mixture was stirred at room temperature for 2 hr. Then the reaction mixture was concentrated to dryness. The residue was partitioned between water and ethyl acetate. NaOH aq. was added to bring pH of the mixture to 10. After excess NH$_4$Cl aq. was added, the mixture was extracted with ethyl acetate. After dried over anhydrous MgSO4, the volatile material was removed under reduced pressure and the residue was purified by chromatography on silica gel using DCM/MeOH (100:1 to 25:1) as eluent to give the desired product (76 mg, 100% yield) as white solid, which was re-purified by chromatography on silica gel using EA/hexane (1:2 to 2:1) followed by EA as eluent to give the desired product (52 mg, 73% yield).

Step 4:

N-{(S)-2-amino-3-[4-(4-chloro-phenoxy)-phenyl]-propyl}-hydroxyamine HCl salt To {(S)-2-[4-(4-chloro-phenoxy)-phenyl]-1-hydroxyaminomethyl-ethyl}-carbamic acid tert-butyl ester (18 mg, 0.046 mmol, 1 eq) in a 2 ml-vial was added 4 N HCl in dioxane (1 ml, 4 mmol, 86 eq.). The mixture was shaken at rt overnight. Then the volatile material was removed to give the desired product (10 mg, 74% yield) as white solid. $^1$H NMR (400 MHz, DMSO-d$_6$) δ 2.94-3.01 (dd, J=6.8, 11.2 Hz, 1H), 3.01-3.05 (dd, J=5.2, 11.2 Hz, 1H), 3.17-3.20 (dd, J=2.4, 11.2 Hz, 1H), 3.37-3.42 (m, 1H), 3.80 (m, 1H), 7.02-7.05 (m, 4H), 7.34-7.35 (d, J=6.8 Hz, 2H), 7.43-7.45 (m, 2H); LCMS (UV, ESI), 294 (M+1), 87% purity.

7.03 (m, 4H), 7.32-7.33 (d, J=6.8 Hz, 2H), 7.42-7.44 (m, 2H), 8.06 (s, brs, 3H); LCMS (UV, ESI), 335 (M+1), 86% purity.

Example 22

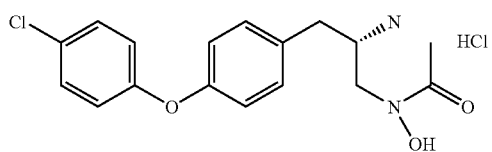

Step 1:

{(S)-1-[(Acetoxy-acetyl-amino)-methyl]-2-[4-(4-chloro-phenoxy)-phenyl]-ethyl}-carbamic acid tert butyl ester To a solution of {(S)-2-[4-(4-chloro-phenoxy)-phenyl]-1-hydroxyaminomethyl-ethyl}-carbamic acid tert-butyl ester (34 mg, 0.087 mmol, 1 eq.) in pyridine (2 ml) was added acetic anhydride (20 mg, 0.173 mmol, 2 eq.). And then the reaction mixture was stirred at room temperature for 1 hr. The reaction mixture was poured into sodium bicarbonate solution (25 ml) and extracted with ethyl acetate (3×15 ml). The combined organics was washed with 1N HCl (3×15 ml). After dried over anhydrous MgSO$_4$, solvent was removed under reduced pressure to give a residue, which was purified by chromatography on silica gel using EA/hexane (1:2 to 1:1) as eluent to give the desired product (44 mg, 100% yield) as gummy.

Step 2:

{(S)-1-[(Acetyl-hydroxy-amino)-methyl]-2-[4-(4-chloro-phenoxy)-phenyl]-ethyl}-carbamic acid tert butyl ester To a solution of {(S)-1-[(Acetoxy-acetyl-amino)-methyl]-2-[4-(4-chloro-phenoxy)-phenyl]-ethyl}-carbamic acid tert butyl ester (27 mg, 0.057 mmol, 1 eq.) in MeOH (2 ml) was added sodium methoxide (15 mg, 0.27 mmol, 4.7 eq.) until pH=10. The mixture was stirred at room temperature for 30 min. Then was poured into saturated NH$_4$Cl solution (15 ml). The mixture was extracted with dichloromethane (3×5 ml). The combined DCM layers were washed with sodium bicarbonate solution (5 ml) and dried over anhydrous MgSO$_4$. Removal of solvent under reduced pressure gave the desired product (20 mg, 81% yield) as an oil.

Step 3:

N-{(S)-2-amino-3-[4-(4-chloro-phenoxy)-phenyl]-propyl}-N-hydroxy-acetamide HCl salt To a 40 ml vial was charged with {(S)-1-[(Acetyl-hydroxy-amino)-methyl]-2-[4-(4-chloro-phenoxy)-phenyl]-ethyl}-carbamic acid tert butyl ester (20 mg, 0.046 mmol, 1 eq.) followed by 4 N HCl (1 ml, 4 mmol, 86 eq.). The mixture was stirred at room temperature for 2 hr. The volatile material was removed under reduced pressure to give the desired product (20 mg, 100% yield) as white solid. $^1$H NMR (400 MHz, DMSO-d$_6$) δ 2.02 (s, 3H), 2.83-2.87 (dd, J=6.4, 11.2 Hz, 1H), 3.17-3.20 (dd, J=4.8, 11.2 Hz, 1H), 3.46-3.87 (m, 4H), 7.0-

Example 23

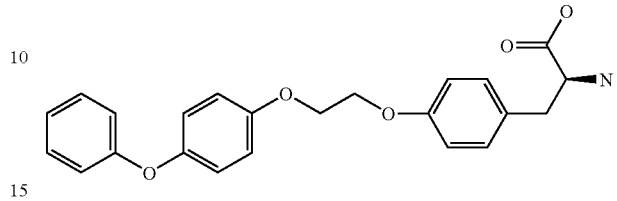

Step 1:

2-(4-Phenoxy-phenoxy)-ethanol

To a solution of 4-Phenoxyphenol (3 g, 16.1 mmol), Potassium carbonate (11.1 g, 80.6 mmol), and 2-Butanone (37.5 mL) was added 2-Bromoethanol (3.14 mL, 44.3 mmol). The resulting mixture was stirred and refluxed at 90° C. overnight under nitrogen. The mixture was poured into 30 mL water solution and extracted with ethyl acetate (EtOAc) (3×10 mL). The combined organic layers were washed with brine (40 mL) and dried over anhydrous Na$_2$SO$_4$. The organic layer was concentrated in vacuo to obtain the crude mixture, which was purified by of silica gel flash chromatography, using EtOAc/hexane (gradient system), to obtain the product (2.3 g, 62%): $^1$H NMR (400 MHz, CDCL$_3$).

Step 2:

1-(2-Bromo-ethoxy)-4-phenoxy-benzene

To a solution of 2-(4-Phenoxy-phenoxy)-ethanol (2.2 g, 9.55 mmol), triphenylphosphine (2.76 g, 10.5 mmol), and dichloromethane (DCM) (36.7 mL) after stirring at 0° C., was added N-Bromosuccinimide (1.87 g, 10.5 mmol). The resulting mixture was stirred at 0° C. for 30 minutes and then at room temperature for 30 minutes. Reaction mixture was concentrated in vacuo to obtain the crude mixture, which was purified by of silica gel flash chromatography, using EtOAc/hexane (gradient system), to obtain the product (2.5 g, 89%): $^1$H NMR (400 MHz, CDCL$_3$).

Step 3:

(S)-2-tert-Butoxycarbonylamino-3-{4-[2-(4-phenoxy-phenoxy)-ethoxy]-phenyl}-propionic acid methyl ester To a solution of 1-(2-Bromo-ethoxy)-4-phenoxy-benzene (2.5 g, 8.53 mmol), potassium carbonate (3.21 g, 23.3 mmol), and N,N-Dimethylformamide (150 mL) was added Boc-L-Tyrosine methyl ester (2.3 g, 7.75 mmol). The mixture was poured into 200 mL water solution and extracted with ethyl acetate (EtOAc) (3×100 mL). The combined organic layers were washed with brine (40 mL) and dried over anhydrous Na$_2$SO$_4$. The organic layer was concentrated in vacuo to obtain the crude mixture, which was purified by of silica gel flash chromatography, using EtOAc/hexane (gradient system), to obtain the product (2.54 g, 59%): $^1$H NMR (400 MHz, CDCL$_3$).

Step 4:

(S)-2-tert-Butoxycarbonylamino-3-{4-[2-(4-phenoxy-phenoxy)-ethoxy]-phenyl}-propionic acid Step 5:

(S)-2-Amino-3-{4-[2-(4-phenoxy-phenoxy)-ethoxy]-phenyl}-propionic acid hydrochloride The results of testing of representative species are shown below:

| Example | EnzIC50 | hWB |
| --- | --- | --- |
| 1 | B | ND |
| 2 | A | ND |
| 3 | A | ND |
| 4 | A | B |
| 5 | B | ND |
| 6 | A | A |
| 7 | ND | ND |
| 8 | B | ND |
| 9 | B | ND |
| 10 | A | ND |
| 11 | A | ND |
| 12 | A | A |
| 13 | A | ND |
| 14 | A | A |
| 15 | A | ND |
| 16 | ND | ND |
| 17 | ND | ND |
| 18 | ND | ND |
| 19 | A | ND |
| 20 | A | A |
| 21 | A | ND |
| 22 | A | A |
| 23 | ND | ND |

A = <5 µM, B = 5-20 µM, C = 20-30 µM, ND = not determined

We claim:

1. A compound of formula

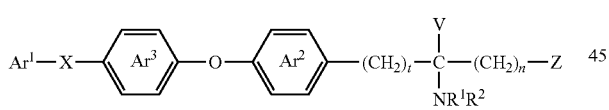

IV wherein

Ar¹ is chosen from
  aryl;
  heteroaryl;
  aryl substituted with from one to three substituents chosen independently from fluorine, chlorine, bromine, haloalkyl, hydroxy, loweralkoxy, carboxy, alkoxycarbonyl, aminocarbonyl, cyano, carbonyl, nitro, amino, alkylamino, dialkylamino, mercapto, alkylthio, alkyl sulfoxide, alkyl sulfone and acylamino; and
  heteroaryl substituted with from one to three substituents chosen independently from halogen, haloalkyl, hydroxy, loweralkoxy, carboxy, alkoxycarbonyl, aminocarbonyl, cyano, carbonyl, nitro, amino, alkylamino, dialkylamino, mercapto, alkylthio, alkyl sulfoxide, alkyl sulfone and acylamino;

Ar² and Ar³ are independently chosen from unsubstituted phenyl and phenyl substituted with from one to three substituents chosen independently from fluorine, chlorine, bromine, haloalkyl, hydroxy, loweralkoxy, carboxy, alkoxycarbonyl, aminocarbonyl, cyano, carbonyl, nitro, amino, alkylamino, dialkylamino, mercapto, alkylthio, alkyl sulfoxide, alkyl sulfone and acylamino;

Z is W or C(=O)W;

W is chosen from $OR^2$, $NR^2R^3$, NHOH, $N(OH)R^6$, N(OH)—C(O)—$R^6$, and —CH(OH)C(O)OH, wherein $R^6$ is alkyl;

X is chosen from —O—, —S(O)$_{0-2}$—, —$CR^4R^5$—, and —C(=O)—;

V is (CH$_2$)$_p$—Z or H;

p is 0-3;

$R^1$, $R^2$, $R^3$, $R^4$ and $R^5$ are independently chosen from H and alkyl; and n is 0-2; and t is 0 or 1.

2. A compound of formula

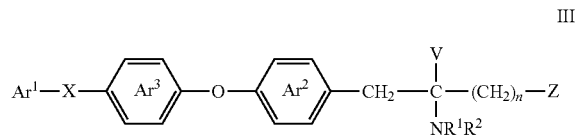

III wherein

Ar¹ is chosen from
  aryl;
  heteroaryl;
  aryl substituted with from one to three substituents chosen independently from fluorine, chlorine, bromine, haloalkyl, hydroxy, loweralkoxy, carboxy, alkoxycarbonyl, aminocarbonyl, cyano, carbonyl, nitro, amino, alkylamino, dialkylamino, mercapto, alkylthio, alkyl sulfoxide, alkyl sulfone and acylamino; and
  heteroaryl substituted with from one to three substituents chosen independently from halogen, haloalkyl, hydroxy, loweralkoxy, carboxy, alkoxycarbonyl, aminocarbonyl, cyano, carbonyl, nitro, amino, alkylamino, dialkylamino, mercapto, alkylthio, alkyl sulfoxide, alkyl sulfone and acylamino;

Ar² and Ar³ are independently chosen from unsubstituted phenyl and phenyl substituted with from one to three substituents chosen independently from fluorine, chlorine, bromine, haloalkyl, hydroxy, loweralkoxy, carboxy, alkoxycarbonyl, aminocarbonyl, cyano, carbonyl, nitro, amino, alkylamino, dialkylamino, mercapto, alkylthio, alkyl sulfoxide, alkyl sulfone and acylamino;

Z is W or C(=O)W;

W is chosen from $OR^2$, $NR^2R^3$, NHOH, $N(OH)R^6$, N(OH)—C(O)—$R^6$, and —CH(OH)C(O)OH, wherein $R^6$ is alkyl;

X is chosen from —O—, —S(O)$_{0-2}$—, —$CR^4R^5$—, and —C(=O)—;

V is (CH$_2$)$_p$—Z or H;

p is 0-3;

$R^1$, $R^2$, $R^3$, $R^4$ and $R^5$ are independently chosen from H and alkyl; and n is 0-2.

3. A compound of formula

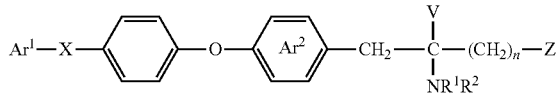

wherein
Ar¹ is chosen from
  aryl;
  heteroaryl;
  aryl substituted with from one to three substituents chosen independently from halogen, haloalkyl, hydroxy, loweralkoxy, carboxy, alkoxycarbonyl, aminocarbonyl, cyano, carbonyl, nitro, amino, alkylamino, dialkylamino, mercapto, alkylthio, alkyl sulfoxide, alkyl sulfone and acylamino; and
  heteroaryl substituted with from one to three substituents chosen independently from halogen, haloalkyl, hydroxy, loweralkoxy, carboxy, alkoxycarbonyl, aminocarbonyl, cyano, carbonyl, nitro, amino, alkylamino, dialkylamino, mercapto, alkylthio, alkyl sulfoxide, alkyl sulfone and acylamino;
Ar² is unsubstituted phenyl or phenyl substituted with from one to three substituents chosen independently from halogen, haloalkyl, hydroxy, loweralkoxy, carboxy, alkoxycarbonyl, aminocarbonyl, cyano, carbonyl, nitro, amino, alkylamino, dialkylamino, mercapto, alkylthio, alkyl sulfoxide, alkyl sulfone and acylamino; and
Z is W or C(=O)W;
W is chosen from OR², NR²R³, NHOH, N(OH)R⁶, N(OH)—C(O)—R⁶, and —CH(OH)C(O)OH, wherein R⁶ is alkyl;
X is chosen from —O—, —S(O)$_{0-2}$—, —CR⁴R⁵—, and —C(=O)—;
V is (CH₂)$_p$—Z or H;
p is 0-3;
R¹, R², R³, R⁴ and R⁵ are independently chosen from H and alkyl; and
n is 0-2.

4. A compound of formula

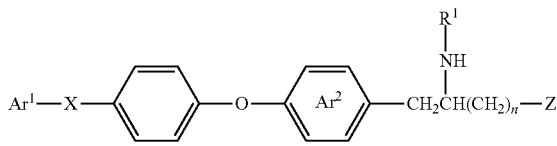

wherein
Ar¹ is chosen from
  aryl;
  heteroaryl;
  aryl substituted with from one to three substituents chosen independently from halogen, haloalkyl, hydroxy, loweralkoxy, carboxy, alkoxycarbonyl, aminocarbonyl, cyano, carbonyl, nitro, amino, alkylamino, dialkylamino, mercapto, alkylthio, alkyl sulfoxide, alkyl sulfone and acylamino; and
  heteroaryl substituted with from one to three substituents chosen independently from halogen, haloalkyl, hydroxy, loweralkoxy, carboxy, alkoxycarbonyl, aminocarbonyl, cyano, carbonyl, nitro, amino, alkylamino, dialkylamino, mercapto, alkylthio, alkyl sulfoxide, alkyl sulfone and acylamino;
Ar² is unsubstituted phenyl or phenyl substituted with from one to three substituents chosen independently from halogen, haloalkyl, hydroxy, loweralkoxy, carboxy, alkoxycarbonyl, aminocarbonyl, cyano, carbonyl, nitro, amino, alkylamino, dialkylamino, mercapto, alkylthio, alkyl sulfoxide, alkyl sulfone and acylamino,
Z is W or C(=O)W;
W is chosen from OR² and NR²R³;
X is chosen from —O—, —S(O)$_{0-2}$—, —CR⁴R⁵—, —C(=O)—, and CH(OH);
R¹, R², R³, R⁴ and R⁵ are independently chosen from hydrogen and alkyl; and
n is 1 or 2.

5. A compound according to claim 4 wherein Ar¹ is chosen from phenyl and phenyl substituted with from one to three substituents chosen independently from halogen, haloalkyl, hydroxy, loweralkoxy, carboxy, alkoxycarbonyl, aminocarbonyl, cyano, carbonyl, nitro, amino, alkylamino, dialkylamino, mercapto, alkylthio, alkyl sulfoxide, alkyl sulfone and acylamino.

6. A compound according to claim 5 wherein Ar¹ and Ar² are phenyl.

7. A compound according to claim 4 wherein R¹ is hydrogen.

8. A compound according to claim 4 wherein X is chosen from —O—, —CH₂— and —C(=O)—.

9. A compound according to claim 4 wherein Z is chosen from —COOH, —COOCH₃, —CONH₂, —OH, —OCH₃ and —NH₂.

10. A compound according to claim 4 wherein Ar¹ and Ar² are phenyl; R¹ is hydrogen; and Z is chosen from —COOH, —COOCH₃, —CONH₂, —OH, —OCH₃ and —NH₂.

11. A pharmaceutical composition comprising a pharmaceutically acceptable carrier and a therapeutically effective amount of at least one compound according to claim 1.

* * * * *